(12) United States Patent
Hoelder et al.

(10) Patent No.: US 7,470,689 B2
(45) Date of Patent: Dec. 30, 2008

(54) 4-BENZIMIDAZOL-2-YLPYRIDAZIN-3-ONE DERIVATIVES

(75) Inventors: Swen Hoelder, Constance (DE); Karl Schoenafinger, Alzenau (DE); David William Will, Kriftel (DE); Hans Matter, Langenselbold (DE); Günter Müller, Sulzbach (DE); Cécile Combeau, Fontenay aux Roses (FR); Christine Delaisi, Saint Maur (FR); Anke Steinmetz, Vitry sur Seine (FR); Ingrid Sassoon, Villejuif (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 11/513,574

(22) Filed: Aug. 31, 2006

(65) Prior Publication Data

US 2007/0173503 A1 Jul. 26, 2007

Related U.S. Application Data

(63) Continuation of application No. PCT/EP2005/002569, filed on Feb. 18, 2005.

(30) Foreign Application Priority Data

Mar. 2, 2004 (DE) .................. 10 2004 010 207

(51) Int. Cl.
  A61K 31/501 (2006.01)
  C07D 401/04 (2006.01)
  C07D 403/04 (2006.01)
  C07D 405/04 (2006.01)
  C07D 409/04 (2006.01)
  C07D 471/04 (2006.01)
  C07D 401/14 (2006.01)
  A61K 31/53 (2006.01)
  C07D 487/04 (2006.01)
  A61P 35/00 (2006.01)

(52) U.S. Cl. ................ 514/252.06; 514/252.04; 514/252.02; 514/243; 514/252.03; 514/236.5; 544/238; 544/236; 544/184; 544/122

(58) Field of Classification Search ............ 514/252.06, 514/252.04, 252.02, 243, 252.03, 236.5; 544/238, 236, 184, 122
See application file for complete search history.

(56) References Cited

U.S. PATENT DOCUMENTS

| | | | |
|---|---|---|---|
| 7,179,811 B2 * | 2/2007 | Janssens et al. | 514/252.04 |
| 7,183,283 B2 * | 2/2007 | Barkoczy et al. | 514/252.03 |
| 7,189,690 B2 | 3/2007 | Rosen et al. | |
| 7,196,109 B2 | 3/2007 | Lesuisse et al. | |
| 7,211,577 B2 * | 5/2007 | Kyotani et al. | 514/236.5 |
| 7,229,776 B2 | 6/2007 | Holvoet et al. | |
| 7,229,999 B2 | 6/2007 | Hebeisen et al. | |
| 7,232,827 B2 | 6/2007 | Lochead et al. | |
| 7,232,828 B2 | 6/2007 | Pershadsingh et al. | |
| 7,232,897 B2 | 6/2007 | Hotamisligil et al. | |
| 7,232,901 B2 | 6/2007 | Mastalerz et al. | |
| 7,232,904 B2 | 6/2007 | Kato et al. | |
| 7,232,906 B2 | 6/2007 | Zhang et al. | |
| 7,232,929 B2 | 6/2007 | Bialer et al. | |
| 7,232,939 B2 | 6/2007 | Herrmann et al. | |
| 2007/0072866 A1 * | 3/2007 | Schoenafinger et al. | 514/252.02 |

FOREIGN PATENT DOCUMENTS

| | | |
|---|---|---|
| CA | 2128464 | 1/1995 |
| EP | 0 639 575 | 2/1995 |
| EP | 1061077 | 12/2000 |
| WO | WO 99/10332 | 3/1999 |
| WO | WO 01/74786 | 10/2001 |
| WO | WO 02/079192 | 10/2002 |
| WO | WO 03/028721 | 4/2003 |
| WO | WO03/035065 A1 | 5/2003 |
| WO | WO 03/059891 | 7/2003 |
| WO | WO 03/066629 | 8/2003 |
| WO | WO 2004/046117 | 6/2004 |
| WO | WO 2004/046130 | 6/2004 |
| WO | WO 2005/085230 | 9/2005 |

OTHER PUBLICATIONS

Axel Huwe et al., Small Molecules as Inhibitors of Cyclin-Dependent Kinases, Angew. Chem. Int. Ed. 2003, 42, pp. 2122-2138.
Mong-Hong Lee et al., Regulators of G1 Cyclin-Dependent Kinases and Cancers, Cancer and Metastasis Reviews 22, 2003, pp. 435-449.

* cited by examiner

*Primary Examiner*—Mark L. Berch
*Assistant Examiner*—Cecilia M Jaisle
(74) *Attorney, Agent, or Firm*—Kelly L. Bender

(57) ABSTRACT

Disclosed are compounds of the general formula (I), where the definition of the substituents A, B, D, E, $R^1$ and $R^2$ are detailed in the description, and the physiologically tolerated salts thereof, a process for the preparation of these compounds and their use as pharmaceuticals.

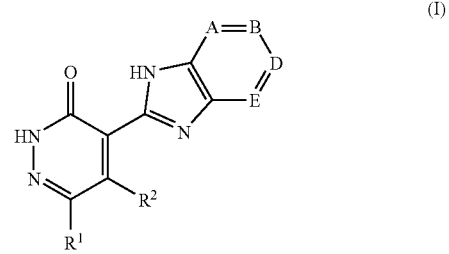

(I)

These compounds are kinase inhibitors, in particular inhibitors of the kinase CDK2 (cyclin-dependent kinase 2).

12 Claims, No Drawings

4-BENZIMIDAZOL-2-YLPYRIDAZIN-3-ONE DERIVATIVES

The invention relates to compounds of the general formula (I), where the definitions of the substituents A, B, D, E, $R^1$ and $R^2$ are detailed in the following text, and to the physiologically tolerated salts thereof, to processes for preparing these compounds and to the use thereof as medicaments.

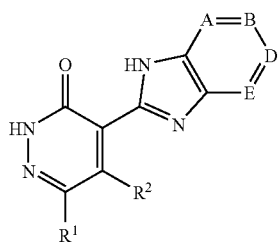

These compounds are kinase inhibitors, in particular inhibitors of the kinase CDK2 (cyclin-dependent kinase 2).

It is known from literature that in the case of neoplastic diseases such as cancer, there is a connection between the therapy of said diseases and the inhibition of CDK2. There are many compounds available, which can be employed as inhibitors of CDK2 and/or other cyclin—dependent kinases such as CDK4 or CDK6 (M. H. Lee et al., Cancer and Metastasis review 22 (2003), 435-449; A. Huwe et al., Angew. Chem. Int. Ed. 42 (2003), 2122-2138; WO 03/028721).

Thus, the international application PCT/EP03/12949 (Publication No. WO2004/046130) discloses pyridazinone derivatives suitable for inhibiting CDK2. The pyridazinone derivatives described therein differ from the compounds of the invention in that, in place of a benzimidazole residue (or a derivative thereof), they have in position 4 of the pyridazinone an amide substituent which can be linked both via the amide carbon atom and via the amide nitrogen atom to the basic pyridazinone structure.

In addition, numerous pyridazinone derivatives are described in the literature but differ from the compounds of the invention through a different substitution pattern and (in some cases) different indications. Thus, it is possible from the general formula disclosed in WO 01/74786 to derive inter alia pyridazinone derivatives which, although they may have a benzimidazole substituent in position 4, on the other hand obligatorily have a sulfonamide group in position 5, in contrast to the compounds of the invention. The compounds described in WO 01/74786 have an inhibitory effect on phosphordiesterase 7 and can be used for the treatment of autoimmune diseases.

WO 03/059891 by contrast discloses pyridazinone derivatives which can be used to treat diseases which is caused or intensified by unregulated p38 MAP kinase and/or TNF activity. The compounds described therein are suitable for example for the treatment of inflammations, of diabetes, of Alzheimer's disease or of cancer. They differ from the compounds of the invention in that the nitrogen in position 2 is mainly substituted by alkyl-, aryl- or heteroaryl and in that a heteroaryl substituent such as benzimidazole is not defined for position 4 of the pyridazinone.

Bicyclic heterocycles having an aggregation inhibiting effect are described in EP-A 0 639 575. It is possible from the general formula (I) specified therein to derive for the bicyclic system having substituent A a benzimidazole derivative which must have at least one further ring nitrogen atom. It is additionally possible to derive for the substituent B theoretically a pyridazinone derivative which in turn must obligatorily be provided with a multi-membered substituent which obligatorily comprises a 1,4-cyclohexylene or 1,4-cyclohex-3-enylene group and a carbonyl group. It is thus evident that the compounds of the invention are not disclosed by EP-A 0 639 575. Compounds explicitly disclosed by EP-A 0 639 575 are not an aspect of the present invention.

There is thus a great need for compounds which have an inhibitory effect on CDK2.

The present invention is therefore based on the object of providing compounds which have these abilities.

The object is achieved by 4-benzimidazol-2-ylpyridazin-3-one derivatives of the following general formula (I)

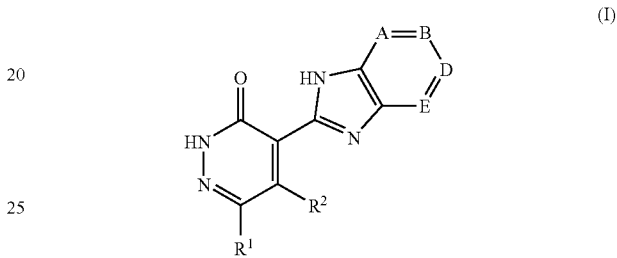

in which the meanings are:
  A is $CR^3$ or N;
  B is $CR^4$ or N;
  D is $CR^5$ or N;
  E is $CR^6$ or N;
  where a maximum of three of the substituents A, B, D and E can simultaneously be N;
  $R^1$ is halogen;
    unsubstituted or at least monosubstituted $C_1$-$C_{10}$-Alkyl, where the substituents are selected from the group consisting of:
      halogen, CN, $NO_2$, —$OR^7$, —$C(O)R^7$, —$C(O)OR^7$, —O—$C(O)R^7$, —$NR^7R^8$, —$NHC(O)R^7$, —$C(O)NR^7R^8$, —$NHC(S)R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, heterocyclyl, trifluoromethyl and trifluoromethoxy,
      and heterocyclyl, aryl and heteroaryl may in turn be at least monosubstituted by $C_1$-$C_6$-alkyl, $C_1$-$C_6$-alkoxy, halogen, trifluoromethyl, trifluoromethoxy or OH;
    unsubstituted or at least monosubstituted aryl or heteroaryl,
      where the substituents are selected from the group consisting of: halogen, —CN, $NO_2$, —$CH_2$—$R^7$, —$OR^7$, —$C(O)R^7$, —$C(O)OR^7$, —O—$C(O)R^7$, —$NR^7R^8$, —$NHC(O)R^7$, —$C(O)NR^7R^8$, —$NHC(S)R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, trifluoromethyl and trifluoromethoxy,
      and aryl and heteroaryl may in turn be at least monosubstituted by $C_1$-$C_6$-alkyl, $C_1$-$C_6$-alkoxy, halogen, trifluoromethyl, trifluoromethoxy or OH;
  $R^2$ is hydrogen or $C_1$-$C_{10}$-alkyl;
  $R^3$ is selected from the group consisting of:
    hydrogen, halogen, —CN, $NO_2$, —$CH_2$—$R^8$, —$OR^8$, —$C(O)R^8$, —$C(O)OR^8$, —O—$C(O)R^8$, —$NR^7R^8$; —$NHC(O)R^8$, —$C(O)NR^7R^8$, —$NHC(S)R^8$, —$C(S)NR^7R^8$, —$SR^8$, —$S(O)R^8$, —$SO_2R^8$, —$NHSO_2R^8$, —$SO_2NR^7R^8$, —$O$—$SO_2R^8$, —$SO_2$—$O$—$R^8$, aryl, heteroaryl, heterocyclyl, trifluoromethyl and trifluoromethoxy, and heterocyclyl, aryl and heteroaryl may in turn be at least monosubstituted by $C_1$-$C_6$-alkyl, $C_1$-$C_6$-alkoxy, oxo, halogen, trifluoromethyl, trifluoromethoxy or OH;

$R^4$ is selected from the group consisting of:
hydrogen, halogen, —CN, $NO_2$, —$CH_2$—$R^8$, —$OR^8$, —$C(O)R^8$, —$C(O)OR^8$, —$O$—$C(O)R^8$, —$NR^7R^8$, —$NHC(O)R^8$, —$C(O)NR^7R^8$, —$NHC(S)R^8$, —$C(S)NR^7R^8$, —$SR^8$, —$S(O)R^8$, —$SO_2R^8$, —$NHSO_2R^8$, —$SO_2NR^7R^8$, —$O$—$SO_2R^8$, —$SO_2$—$O$—$R^8$, aryl, heteroaryl, heterocyclyl, trifluoromethyl and trifluoromethoxy, and heterocyclyl, aryl and heteroaryl may in turn be at least monosubstituted by $C_1$-$C_6$-alkyl, $C_1$-$C_6$-alkoxy, oxo, halogen, trifluoromethyl, trifluoromethoxy or OH;

$R^5$ is selected from the group consisting of:
hydrogen, halogen, —CN, $NO_2$, —$CH_2$—$R^8$, —$OR^8$, —$C(O)R^8$, —$C(O)OR^8$, —$O$—$C(O)R^8$, —$NR^7R^8$; —$NHC(O)R^8$, —$C(O)NR^7R^8$, —$NHC(S)R^8$, —$C(S)NR^7R^8$, —$SR^8$, —$S(O)R^8$, —$SO_2R^8$, —$NHSO_2R^8$, —$SO_2NR^7R^8$, —$O$—$SO_2R^8$, —$SO_2$—$O$—$R^8$, aryl, heteroaryl, heterocyclyl, trifluoromethyl and trifluoromethoxy, and heterocyclyl, aryl and heteroaryl may in turn be at least monosubstituted by $C_1$-$C_6$-alkyl, $C_1$-$C_6$-alkoxy, oxo, halogen, trifluoromethyl, trifluoromethoxy or OH;

$R^6$ is selected from the group consisting of:
hydrogen, halogen, —CN, $NO_2$, —$CH_2$—$R^8$, —$OR^8$, —$C(O)R^8$, —$C(O)OR^8$, —$O$—$C(O)R^8$, —$NR^7R^8$; —$NHC(O)R^8$, —$C(O)NR^7R^8$, —$NHC(S)R^8$, —$C(S)NR^7R^8$, —$SR^8$, —$S(O)R^8$, —$SO_2R^8$, —$NHSO_2R^8$, —$SO_2NR^7R^8$, —$O$—$SO_2R^8$, —$SO_2$—$O$—$R^8$, aryl, heteroaryl, heterocyclyl, trifluoromethyl and trifluoromethoxy, and heterocyclyl, aryl and heteroaryl may in turn be at least monosubstituted by $C_1$-$C_6$-alkyl, $C_1$-$C_6$-alkoxy, oxo, halogen, trifluoromethyl, trifluoromethoxy or OH;

$R^7$ is H;
unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl, where the substituents are selected from the group consisting of: heteroaryl, heterocyclyl, aryl, oxo, halogen, OH, $C_1$-$C_{10}$-alkoxy, ($C_1$-$C_{10}$-alkyl)thio-, COOH, —COO—($C_1$-$C_6$-alkyl), —$CONH_2$, trifluoromethyl, trifluoromethoxy; CN, $NH_2$, ($C_1$-$C_{10}$-alkyl)amino- and di-($C_1$-$C_{10}$-alkyl)amino-, and heterocyclyl, aryl and heteroaryl may in turn be at least monosubstituted by $C_1$-$C_6$-alkyl, $C_1$-$C_6$-alkoxy, oxo, trifluoromethyl, trifluoromethoxy, fluorine, chlorine or OH;

$R^8$ is H;
unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl, where the substituents are selected from the group consisting of: heteroaryl, heterocyclyl, aryl, halogen, OH, oxo, $C_1$-$C_{10}$-alkoxy, ($C_1$-$C_{10}$-alkyl)thio-, COOH, —COO—($C_1$-$C_6$-alkyl), —$CONH_2$, trifluoromethyl, trifluoromethoxy; CN, $NH_2$, ($C_1$-$C_{10}$-alkyl)amino- and di-($C_1$-$C_{10}$-alkyl)amino-, and heterocyclyl, aryl and heteroaryl may in turn be at least monosubstituted by $C_1$-$C_6$-alkyl, $C_1$-$C_6$-alkoxy, oxo, trifluoromethyl, trifluoromethoxy, fluorine, chlorine or OH;

Heteroaryl is a 5 to 10-membered, aromatic, mono- or bicyclic heterocycle which comprises one or more heteroatoms selected from N, O and S;

Aryl is a 5 to 10-membered, aromatic, mono- or bicyclic system;

Heterocyclyl is a 5 to 10-membered, nonaromatic, mono- or bicyclic heterocycle which comprises one or more heteroatoms selected from N, O and S;

or a physiologically tolerated salt thereof.

The above meanings of the substituents $R^1$ to $R^8$, A, B, D, E, heteroaryl, heterocyclyl and aryl are the basic meanings (definitions) of the respective substituents.

If in the compounds of formula (I) groups, fragments, residues or substituents such as, for example, aryl, heteroaryl, alkyl, alkoxy etc., are present several times, they all independently from each other have the meanings indicated and may hence, in each individual case, be identical with or different from each other. The following comments apply to (for example) aryl as well as to any other residue independently from its classification as aryl group, -substituent, -fragment or -residue. One example is the di($C_1$-$C_6$-alkyl)amino group in which the alkyl substituents may be identical or different (for instance 2×ethyl or 1×propyl and 1×hexyl).

If in the above-mentioned definitions of compounds according to formula (I) a substituent, for example aryl, is unsubstituted or at least monosubstituted with a group of further substituents, for example, $C_1$-$C_6$-alkyl, $C_1$-$C_6$-alkoxy, halogen etc., it applies in such cases, where there is a polysubstitution of aryl, that the selection from the group of further substituents is independent from each other. Thus, all combinations of further substituents are comprised in the case of, for example, a disubstitution of aryl. Therefore, aryl may be substituted twice with ethyl, aryl may be monosubstituted with methyl or ethoxy, aryl may be monosubstituted with ethyl or fluoro, respectively, aryl may be substituted twice with methoxy, etc.

Alkyl residues may be linear or branched, acyclic or cyclic. This also applies when they are part of other groups, for example in alkoxy groups, ($C_1$-$C_{10}$-alkyl—O—), alkoxycarbonyl groups or amino groups, or when they are substituted.

Examples for alkyl groups are: methyl, ethyl, propyl, butyl, pentyl, hexyl, humpty, octyl, nonyl, decyl. This comprises both the n-isomers of these residues and isopropyl, isobutyl, isopentyl, sec-butyl, tert-butyl, neopentyl, 3,3-dimethylbutyl etc. Furthermore, unless stated otherwise, the term alkyl here also includes unsubstituted alkyl residues as well as alkyl residues which are substituted by one or more, for example one, two, three or four, identical or different residues, for example aryl, heteroaryl, alkoxy or halogen. The additional substituents may be present in any desired position of the alkyl residue. The term alkyl here also includes cycloalkyl residues and cycloalkyl-alkyl residues (alkyl substituted by cycloalkyl), where cycloalkyl contains at least three carbon atoms. Examples for such cycloalkyl residues are cyclopropyl, cyclobutyl, cyclopentyl, cyclohexyl, cycloheptyl, cyclooctyl, cyclononyl and cyclodecyl. Optionally, these may also be polycyclic ring systems, such as decalinyl, norbornanyl, bornanyl or adamantanyl. The cycloalkyl residues may be unsubstituted or optionally substituted by one or more further residues, as exemplified above in the case of the alkyl residues.

Examples for alkenyl and alkynyl groups are vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl. The term alkenyl here also expressly includes cycloalkenyl residues and cycloalkenyl-alkyl-residues (alkyl substituted by cycloalkenyl) containing at least three carbon atoms. Examples for cycloalkenyl are cyclopentenyl, cyclohexenyl, cycloheptenyl and cyclooctenyl.

The alkenyl residues may have 1 to 3 conjugated or unconjugated double bonds (thus also alk-dienyl- as well as alktrienyl-residues), preferably one double bond in a straight or branched chain; the same applies to alkynyl residues in respect of triple bonds. The alkenyl and alkynyl residues may be unsubstituted or optionally substituted by one or more further residues, as exemplified above in the case of the alkyl residues.

Unless stated otherwise, the above-mentioned aryl, heteroaryl and heterocyclyl residues may be unsubstituted or may carry one or more, for example one, two, three or four of the substituents indicated in the above definition, which substituents may be in any desired position. In monosubstituted phenyl residues, for example, the substituent may be in the 2-position, the 3-position or the 4-position, in disubstituted phenyl residues the substituents may be in 2,3-position, 2,4-position, 2,5-position, 2,6-position, 3,4-position or 3,5-position. In trisubstituted phenyl residues the substituents may be in 2,3,4-position, 2,3,5-position, 2,3,6-position, 2,4,5-position, 2,4,6-position or 3,4,5-position. In fourfold substituted phenyl residues, the substituents may be in the 2,3,4,5-position, the 2,3,4,6-position, or the 2,3,5,6-position.

The above definitions as well as the following definitions relating to monovalent residues equally apply to the divalent residues phenylene, naphthylene and heteroarylene. Those divalent residues (fragments) may be attached to the adjacent groups for any ring carbon atom. In the case of a phenylene residue, this may be in 1,2-position (ortho-phenylene), 1,3-position (meta-phenylene) or 1,4-position (para-phenylene). In the case of 5-membered aromatics containing one heteroatom such as, for example, thiophene or furan, the two free bonds may be in 2,3-position, 2,4-position, 2,5-position or 3,4-position. A divalent residue derived from a 6-membered aromatic with a heteroatom, such as for example pyridine, may be a 2,3-, 2,4-, 2,5-, 2,6-, 3,4- or 3,5-pyridinediyl residue. In the case of unsymmetrical divalent residues the present invention includes all positional isomers, i. e., in the case of a 2,3-pyridinediyl residue, for example, it includes the compound in which the one adjacent group is present in the 2-position and the other adjacent group is present in the 3-position as well as the compound in which the one adjacent group is present in the 3-position and the other adjacent group is present in the 2-position.

Unless stated otherwise, heteroaryl residues, heteroarylene residues, heterocyclyl residues, heterocyclylene residues and rings which are formed by two groups bonded to a nitrogen are preferably derived from completely saturated, partially unsaturated or completely unsaturated heterocycles (i.e. heterocycloalkanes, heterocycloalkenes, heteroaromatics), which contain one, two, three or four heteroatoms, which may be identical or different; more preferably they are derived from heterocycles which contain one, two, or three, in particular one or two, heteroatoms, which may be identical or different. Unless stated otherwise, the heterocycles may be monocyclic or polycyclic, for example monocyclic, bicyclic or tricyclic. Preferably they are monocyclic or bicyclic. The rings preferably are 5-membered rings, 6-membered rings or 7-membered rings particularly preferably 5-membered rings or 6-membered rings. In the case of polycyclic heterocycles containing two or more heteroatoms, they may all be within the same ring or within different rings.

According to the present invention, heteroaryl is a residue derived from mono- or bicyclic aromatic heterocycles. Examples of heteroaryl are: pyrrolyl, furanyl (=furyl), thiophenyl (=thienyl), imidazolyl, pyrazolyl, 1,2,3-triazolyl, 1,2,4-triazolyl, 1,3-oxazolyl (=oxazolyl), 1,2-oxazolyl (=isoxazolyl), oxadiazolyl, 1,3-thiazolyl (=thiazolyl), 1,2-thiazolyl (=isothiazolyl), tetrazolyl, pyridinyl (=pyridyl) pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, quinolinyl, isoquinolinyl, quinazolinyl, quinoxalinyl, phthalazinyl, thienothiophenyl, 1,8-naphthyridinyl, other naphthyridinyls, pteridinyl or thiazolo[3,2-b][1,2,4]-tiazolyl. In the case it is not a monocycle, each of the above heteroaryls includes for its second ring also its saturated form (perhydro form) or its partially unsaturated form (for example in the dihydro form or the tetrahydro form) or its maximally unsaturated (nonaromatic form) where the respective forms are known and stable. The term "heteroaryl" as used herein comprises therefore, for example, bicyclic residues in which both rings are aromatic as well as bicyclic residues in which only one ring is aromatic. Such examples for heteroaryl are: 3H-indolinyl, 2(1H)-quinolinonyl, 4-oxo-1,4-dihydroquinolinyl, 2H-1-oxoisoquinolinyl, 1,2-dihydroquinolinyl, 3,4-dihydroquinolinyl, 1,2-dihydroisoquinolinyl, 3,4-dihydroisoquinolinyl, chromonyl, chromanyl, 1,3-benzodioxolyl, oxindolyl, 1,2,3,4-tetrahydroisoquinolinyl, 1,2,3,4-tetrahydroquinolinyl, 5,6-dihydroquinolyl, 5,6-dihydroisoquinolyl, 5,6,7,8-tetrahydroquinolinyl or 5,6,7,8-tetrahydroisoquinolyl.

According to the present invention, heterocyclyl is a residue derived from mono-or bicyclic nonaromatic heterocycles. Nonaromatic heterocycles comprise in the following especially heterocycloalkanes (completely saturated heterocycles) as well as heterocycloalkenes (partially unsaturated heterocycles). In the case of heterocycloalkenes there are also included compounds having two or more double bonds, which may optionally be conjugated. Examples of heterocyclyl are: pyrrolidinyl, piperidinyl, piperazinyl, imidazolidinyl, pyrazolidinyl, isothiazolidinyl, thiazolidinyl, isoxazolidinyl, oxazolidinyl, tetrahydrofuranyl, tetrahydrothiophenyl, 1,3-dioxolanyl, 1,4-dioxinyl, pyranyl, thiopyranyl, tetrahydro-1,2-oxazinyl, tetrahydro-1,3-oxazinyl, morpholinyl, thiomorpholinyl, 1,2-thiazinyl, 1,3-thiazinyl, 1,4-thiazinyl, azepinyl, 1,2-diazepinyl, 1,3-diazepinyl, 1,4-diazepinyl, 1,3-oxazepinyl, 1,3-thiazepinyl, azepanyl, 2-oxo-azepanyl, 1,2,3,4-tetrahydropyridinyl, 1,2-dihydropyridinyl, 1,4-dihydropyridinyl, 1,2,3,6-tetrahydropyridinyl, 4(3H)-pyrimidonyl, 1,4,5,6-tetrahydropyrimidinyl, 2-pyrrolinyl, 3-pyrrolinyl, 2-imidazolinyl, 2-pyrazolinyl, 3,4-dihydro-2H-pyranyl, dihydrofuranyl, 7-oxabicyclo[2.2.1]heptenyl, dihydrothiophenyl or dihydrothiopyranyl. The degree of saturation of heterocyclic groups is indicated in their individual definitions.

Substituents which may be derived from these heterocycles may be attached via any suitable carbon atom and be provided with further substituents. Residues derived from nitrogen heterocycles may carry a hydrogen atom or another substituent on a corresponding nitrogen atom, and examples include pyrrole, imidazole, pyrrolidine, morpholine, piperazine residues, etc. Those nitrogen heterocyclic residues may also be attached via the ring nitrogen atom, in particular if the respective heterocyclic residue is bonded to a carbon atom. For example, a thienyl residue may be present as 2-thienyl or 3-thienyl, a piperidinyl residue as 1-piperidinyl (=piperidino), 2-piperidinyl, 3-piperidinyl or 4-piperidinyl. Suitable nitrogen heterocycles may also be present as N-oxides or as quarternary salts containing a counter ion which is derived from a physiologically acceptable acid. Pyridyl residues, for example, may be present as pyridine N-oxides. Suitable sulfur-containing heterocycles may be present as S-oxide or S—S-dioxide.

According to the present invention, aryl is a residue derived from mono- or bicyclic aromatics, which do not contain any ring heteroatoms. Where it is not a monocycle, the term aryl includes for its second cycle also its saturated form (perhydro form) or its partially unsaturated form (for example in the dihydro form or the tetrahydro form) where the respective forms are known and stable. The term aryl as used herein comprises therefore, for example, bicyclic residues in which both rings are aromatic as well as bicyclic residues in which only one ring is aromatic. Examples for aryl are: phenyl, naphthyl, indanyl, 1,2-dihydronaphthenyl, 1,4-dihydronaphthenyl, indenyl or 1,2,3,4-tetrahydronaphthyl.

Arylalkyl means an alkyl residue, which in turn is substituted by an aryl residue. Heteroarylalkyl means an alkyl residue, which in turn is substituted by a heteroaryl residue. Heterocyclylalkyl means an alkyl residue, which in turn is substituted by a heterocyclyl residue. For the definitions and possible substitutions of alkyl, heteroaryl, heterocyclyl and aryl it is referred to the above-mentioned definitions.

Halogen is fluorine, chlorine, bromine or iodine, preferably fluorine, chlorine or bromine, most preferably fluorine or chlorine.

The present invention includes all stereoisomeric forms of the compounds of the formula (I). Asymmetrical carbon atoms that are present in the compounds of formula (I) all independently of one another have S configuration or R configuration. The invention includes all possible enantiomers and diastereomers and mixtures of two or more stereoisomers, for example mixtures of enantiomers and/or diastereomers, in all amounts and ratios. Thus, compounds according to the present invention which may exist as enantiomers may be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are an object of the present invention. The preparation of individual stereoisomers may be carried out, if desired, by separation of a mixture by customary methods, for example by chromatography or crystallization, by the use of stereochemically uniform starting materials for the synthesis or by stereoselective synthesis. Optionally, a derivatization may be carried out before a separation of stereoisomers. The separation of a mixture of stereoisomers may be carried out at the stage of the compounds of the formula (I) or at the stage of an intermediate during the synthesis. The present invention also includes all tautomeric forms of the compounds of formula (I), in particular keto-enol tautomerism, i.e. the respective compounds may be present either in their keto form or in their enol form or in mixtures thereof in all ratios.

Where the compounds according to formula (I) contain one or more acidic or basic groups, the invention also comprises their corresponding physiologically or toxicologically acceptable salts.

Physiologically acceptable salts are particularly suitable for medical applications, due to their greater solubility in water compared with the starting or base compounds. Said salts must have a physiologically acceptable anion or cation. Suitable physiologically acceptable acid addition salts of the compounds of the invention are salts of inorganic acids such as hydrochloric acid, hydrobromic acid, phosphoric acid, metaphosphoric acid, nitric acid, sulfonic acid and sulfuric acid and also of organic acids such as, for example, acetic acid, theophyllineacetic acid, methylene-bis-b-oxynaphthonic acid, benzenesulfonic acid, benzoic acid, citric acid, ethanesulfonic acid, salicylic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically unacceptable anion are likewise included within the scope of the present invention as useful intermediates for preparing or purifying pharmaceutically acceptable salts and/or for use in nontherapeutic applications, for example in-vitro applications.

If the compounds of the formula (I) simultaneously contain acidic and basic groups in the same molecule, the invention also includes, in addition to the salt forms mentioned, inner salts or betaines (zwitterions).

The respective salts of the compounds according to the formula (I) may be obtained by customary methods which are known to the person skilled in the art like, for example by reacting these with an organic or inorganic acid or base in a solvent or dispersant, or by anion exchange or cation exchange with other salts.

The present invention furthermore includes all solvates of compounds of the formula (I), for example hydrates or adducts with alcohols, active metabolites of the compounds of the formula (I), and also derivatives, which contain physiologically tolerable and cleavable groups, for example esters or amides.

The term "physiologically functional derivative" used herein relates to any physiologically acceptable derivative of an inventive compound of the formula I, for example an ester which on administration to a mammal, for example humans, is capable of forming (directly or indirectly) a compound of the formula I or an active metabolite thereof.

The physiologically functional derivatives also include prodrugs of the compounds of the invention. Such prodrugs may be metabolized in vivo to a compound of the invention. These prodrugs may or may not be active themselves and are also object of the present invention.

The compounds of the invention may also be present in various polymorphous forms, for example as amorphous and crystalline polymorphous forms. All polymorphous forms of the compounds of the invention are included within the scope of the invention and are another aspect of the invention.

Preferred compounds of the general formula (I) are the compounds in which one, more than one or all of the substituents $R^1$ to $R^8$, A, B, D, E, heteroaryl, heterocyclyl and aryl detailed above have independently of one another the meanings (definitions) detailed below, and the present invention relates to all possible combinations of preferred, more preferred, even more preferred, particularly preferred and very particularly preferred meanings (definitions), likewise in combination with the substituents in their basic meaning.

A is preferably $CR^3$;
B is preferably $CR^4$;
D is preferably $CR^5$; and
E is preferably $CR^6$.

If not every one of the substituents A, B, D and E has its preferred meaning, then preferably only two of the substituents A, B, D and E are equal to N; more preferably only one of the substituents A, B, D and E is equal to N; even more preferably, only the substituent B is equal to N.

$R^1$ is preferably:
- fluorine; chlorine; bromine;
- unsubstituted or at least monosubstituted $C_1$-$C_6$-alkyl,
  - where the substituents are selected from the group consisting of: halogen, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, heterocyclyl, trifluoromethyl and trifluoromethoxy,
  - and heterocyclyl, aryl and heteroaryl may in turn be at least monosubstituted by $C_1$-$C_6$-alkyl, $C_1$-$C_6$-alkoxy, halogen, trifluoromethyl, trifluoromethoxy or OH;
- unsubstituted or at least monosubstituted aryl or heteroaryl,
  - where the substituents are selected from the group consisting of: halogen, —$CH_2$—$R^7$, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, trifluoromethyl and trifluoromethoxy,
  - and aryl and heteroaryl may in turn be at least monosubstituted by $C_1$-$C_6$-alkyl, $C_1$-$C_6$-alkoxy, halogen, trifluoromethyl, trifluoromethoxy or OH.

$R^1$ is more preferably:
- chlorine;
- unsubstituted or at least monosubstituted $C_1$-$C_6$-alkyl,
  - where the substituents are selected from the group consisting of: fluorine, chlorine, OH, $C_1$-$C_6$-alkoxy, $NH_2$, ($C_1$-$C_6$-alkyl)amino-, di-($C_1$-$C_6$-alkyl) amino-, —NH(heterocyclyl-($C_1$-$C_6$-alkyl-)), —NH(aryl-($C_1$-$C_6$-alkyl-)), heterocyclyl, aryl and heteroaryl,
  - and heterocyclyl, aryl and heteroaryl may in turn be at least monosubstituted by $C_1$-$C_4$-alkyl, $C_1$-$C_4$-alkoxy, fluorine, chlorine, trifluoromethyl, trifluoromethoxy or OH;
- unsubstituted or at least monosubstituted phenyl, pyridinyl, pyrimidinyl, pyrazolyl, thiophenyl, oxazolyl, isoxazolyl, benzo[b]thiophenyl, 1,3-benzodioxolyl or thiazolo[3,2-b][1,2,4]-triazolyl,
  - where the substituents are selected from the group consisting of: halogen, —$CH_2$—$R^7$, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, trifluoromethyl and trifluoromethoxy,
  - and aryl and heteroaryl may in turn be at least monosubstituted by $C_1$-$C_6$-alkyl, $C_1$-$C_6$-alkoxy, halogen, trifluoromethyl, trifluoromethoxy or OH.

$R^1$ is even more preferably:
- unsubstituted or at least monosubstituted phenyl, pyridinyl, pyrimidinyl, pyrazolyl, thiophenyl, oxazolyl, isoxazolyl, benzo[b]thiophenyl, benzodioxolyl or thiazolo[3,2-b][1,2,4]-triazolyl,
  - where the substituents are selected from the group consisting of: halogen, —$CH_2$—$R^7$, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, trifluoromethyl and trifluoromethoxy,
  - and aryl and heteroaryl may in turn be at least monosubstituted by $C_1$-$C_6$-alkyl, $C_1$-$C_6$-alkoxy, halogen, trifluoromethyl, trifluoromethoxy or OH.

$R^1$ is much more preferably:
- unsubstituted or at least monosubstituted phenyl, pyridinyl, pyrimidinyl, pyrazolyl, thiophenyl, oxazolyl, isoxazolyl, benzo[b]thiophenyl, benzodioxolyl or thiazolo[3,2-b][1,2,4]-triazolyl,
  - where the substituents are selected from the group consisting of: halogen, $C_1$-$C_6$-alkyl, phenyl-($C_1$-$C_6$-alkyl)-, —OH, $C_1$-$C_6$-alkoxy, ($C_1$-$C_6$-alkyl)thio-, —O-phenyl, —C(O)OH, —C(O)O—($C_1$-$C_6$-alkyl), —$NH_2$, —$N(C_1$-$C_6$-alkyl)$_2$, —NH($C_1$-$C_6$-alkyl), —NH(amino-($C_1$-$C_6$-alkyl-)), —NH(($C_1$-$C_6$-alkyl)amino-($C_1$-$C_6$-alkyl-)), —NH(di-($C_1$-$C_6$-alkyl)amino-($C_1$-$C_6$-alkyl-)), —NH(heterocyclyl-($C_1$-$C_6$-alkyl-)), —NH(heteroaryl-($C_1$-$C_6$-alkyl-)), —NH(phenyl-($C_1$-$C_6$-alkyl-)), —C(O)$NH_2$, —C(O)NH—($C_1$-$C_6$-alkyl), trifluoromethyl, trifluoromethoxy, phenyl and heteroaryl,
  - and heterocyclyl, phenyl and heteroaryl may in turn be at least monosubstituted by $C_1$-$C_3$-alkyl, $C_1$-$C_3$-alkoxy, fluorine, chlorine, trifluoromethyl, trifluoromethoxy or OH.

$R^1$ is particularly preferably:
- unsubstituted or at least monosubstituted phenyl, pyrazolyl, thiophenyl, pyridinyl or pyrimidinyl,
  - where the substituents are selected from the group consisting of: $C_1$-$C_4$-alkyl, OH, $C_1$-$C_4$-alkoxy, ($C_1$-$C_4$-alkyl)thio-, trifluoromethyl, trifluoromethoxy and ($C_1$-$C_4$-alkyl)amino-,
  - and ($C_1$-$C_4$-alkyl)amino- may in turn be monosubstituted by phenyl, piperazinyl, piperidinyl or morpholinyl.

$R^1$ is very particularly preferably:
- pyridin-4-yl, 2-ethylaminopyrimidin-4-yl, 2-(2-morpholin-4-ylethylamino)-pyrimidin-4-yl, 2-methylaminopyrimidin-4-yl, 6-methyl-2-(2-morpholin-4-ylethylamino)pyrimidin-4-yl, 2-(1-phenylethylamino)pyrimidin-4-yl, 3-methoxy-4-hydroxyphenyl or 4-butylaminopyrimidin-4-yl.

$R^2$ is preferably hydrogen or $C_1$-$C_6$-alkyl; $R^2$ is particularly preferably hydrogen.

$R^3$ is preferably selected from the group consisting of:
- hydrogen, halogen, —CN, —$CH_2$—$R^8$, —$OR^8$, —$C(O)R^8$, —$C(O)OR^8$, —$NR^8H$, —$NR^8(C_1$-$C_6$-alkyl-), —$C(O)NR^8H$, —$SR^8$, —$SO_2NR^8H$, —$SO_2R^8$, aryl, heteroaryl, heterocyclyl, trifluoromethyl and trifluoromethoxy,
- and heterocyclyl, aryl and heteroaryl may in turn be at least monosubstituted by $C_1$-$C_6$-alkyl, $C_1$-$C_6$-alkoxy, oxo, halogen, trifluoromethyl, trifluoromethoxy or OH.

$R^3$ is more preferably selected from the group consisting of:
- hydrogen, fluorine, chlorine, bromine, —CN, —$CH_2$—$R^8$, —$OR^8$, —$C(O)R^8$, —$C(O)OR^8$, —$NR^8H$, —$NR^8(C_1$-$C_6$-alkyl-), —$C(O)NR^8H$, —$SR^8$, —$SO_2NR^8H$, —$SO_2$—$R^8$, heterocyclyl, trifluoromethyl and trifluoromethoxy,
- and heterocyclyl may in turn be at least monosubstituted by $C_1$-$C_6$-alkyl, $C_1$-$C_6$-alkoxy, halogen, trifluoromethyl, trifluoromethoxy or OH.

$R^3$ is much more preferably selected from the group consisting of:
- hydrogen, fluorine, chlorine, bromine, —CN, $C_1$-$C_6$-alkyl, phenyl-($C_1$-$C_6$-alkyl)-, —OH, $C_1$-$C_6$-alkoxy, —O-phenyl, —C(O)OH, —C(O)O—($C_1$-$C_6$-alkyl), —$NR^8H$, —$NR^8(C_1$-$C_6$-alkyl-), —$C(O)NR^8H$, heterocyclyl, trifluoromethyl and trifluoromethoxy,
- and heterocyclyl and phenyl may in turn be at least monosubstituted by $C_1$-$C_6$-alkyl, $C_1$-$C_6$-alkoxy, halogen, trifluoromethyl, trifluoromethoxy or OH.

$R^3$ is even much more preferably selected from the group consisting of:
- hydrogen, fluorine, chlorine, bromine, —CN, $C_1$-$C_6$-alkyl, —OH, $C_1$-$C_6$-alkoxy, —C(O)OH, —C(O)O—($C_1$-$C_6$-alkyl), —$NH_2$, —$N(C_1$-$C_6$-alkyl)$_2$, —NH($C_1$-$C_6$-alkyl), —NH(amino-($C_1$-$C_6$-alkyl-)), —NH(hydroxy-($C_1$-$C_6$-alkyl-)), —NH(($C_1$-$C_6$-alkyl)-amino-($C_1$-$C_6$-alkyl-)), —NH(di-($C_1$-$C_6$-alkyl)amino-($C_1$-$C_6$-alkyl-)), —NH(heterocyclyl-($C_1$-$C_6$-alkyl-)), —NH(heteroaryl-($C_1$-$C_6$-alkyl-)), —NH(phenyl-($C_1$-$C_6$-alkyl-)), —C(O)$NH_2$, —C(O)NH—($C_1$-$C_6$-alkyl), —C(O)N($C_1$-$C_6$- alkyl)$_2$, —C(O)NH(C$_1$-C$_6$-alkyl), —C(O)NH(amino-(C$_1$-C$_6$-alkyl)), —C(O)NH(hydroxy-(C$_1$-C$_6$-alkyl-)), —C(O)NH((C$_1$-C$_6$-alkyl)amino-(C$_1$-C$_6$-alkyl-)), —C(O)NH(di-(C$_1$-C$_6$-alkyl)amino-(C$_1$-C$_6$-alkyl-)), —C(O)NH(heterocyclyl-(C$_1$-C$_6$-alkyl-)), —C(O)NH (heteroaryl-(C$_1$-C$_6$-alkyl-)), —C(O)NH(phenyl-(C$_1$-C$_6$-alkyl-)), heterocyclyl, trifluoromethyl and trifluoromethoxy, and heteroaryl, heterocyclyl and phenyl may in turn be at least monosubstituted by C$_1$-C$_6$-alkyl, C$_1$-C$_6$-alkoxy, halogen, trifluoromethyl, trifluoromethoxy or OH.

$R^3$ is particularly preferably selected from the group consisting of:

hydrogen, fluorine, chlorine, bromine, —CN, —C(O)NH (2-cyclohexylamino-ethyl-), —C(O)NH(3-(4-methylpiperazin-1-yl)-propyl-), —C(O)NH(3-hydroxy-propyl-), —C(O)NH(3-cyclohexylaminopropyl-), methyl, ethyl and trifluoro-methyl.

$R^3$ is very particularly preferably selected from the group consisting of:

hydrogen, fluorine, chlorine, bromine, methyl and ethyl;

$R^4$ is preferably selected from the group consisting of:

hydrogen, halogen, —CN, —CH$_2$—R$^8$, —OR$^8$, —C(O)R$^8$, —C(O)OR$^8$, —NR$^8$H, —NR$^8$(C$_1$-C$_6$-alkyl-), —C(O)NR$^8$H, —SR$^8$, —SO$_2$NR$^8$H, —SO$_2$—R$^8$, aryl, heteroaryl, heterocyclyl, trifluoromethyl and trifluoromethoxy, and heterocyclyl, aryl and heteroaryl may in turn be at least monosubstituted by C$_1$-C$_6$-alkyl, C$_1$-C$_6$-alkoxy, oxo, halogen, trifluoromethyl, trifluoromethoxy or OH;

$R^4$ is more preferably selected from the group consisting of:

hydrogen, fluorine, chlorine, bromine, —CN, —SO$_2$NR$^8$H, —SO$_2$—R$^8$, —CH$_2$—R$^8$, —OR$^8$, —C(O)R$^8$, —C(O)OR$^8$, —NR$^8$H, —NR$^8$(C$_1$-C$_6$-alkyl-), —C(O)NR$^8$H, —SR$^8$, heterocyclyl, trifluoromethyl and trifluoromethoxy, and heterocyclyl may in turn be at least monosubstituted by C$_1$-C$_6$-alkyl, C$_1$-C$_6$-alkoxy, halogen, trifluoromethyl, trifluoromethoxy or OH;

$R^4$ is much more preferably selected from the group consisting of:

hydrogen, fluorine, chlorine, bromine, —CN, C$_1$-C$_6$-alkyl, phenyl-(C$_1$-C$_6$-alkyl)-, —OH, C$_1$-C$_6$-alkoxy, —O-phenyl, —C(O)OH, —C(O)O—(C$_1$-C$_6$-alkyl), —NR$^8$H, —NR$^8$(C$_1$-C$_6$-alkyl-), —C(O)NR$^8$H, heterocyclyl, trifluoromethyl and trifluoromethoxy, and heterocyclyl and phenyl may in turn be at least monosubstituted by C$_1$-C$_6$-alkyl, C$_1$-C$_6$-alkoxy, halogen, trifluoromethyl, trifluoromethoxy or OH;

$R^4$ is even much more preferably selected from the group consisting of:

hydrogen, fluorine, chlorine, bromine, —CN, C$_1$-C$_6$-alkyl, —OH, C$_1$-C$_6$-alkoxy, —C(O)OH, —C(O)O—(C$_1$-C$_6$-alkyl), —NH$_2$, —N(C$_1$-C$_6$-alkyl)$_2$, —NH(C$_1$-C$_6$-alkyl), —NH(amino-(C$_1$-C$_6$-alkyl-)), —NH(hydroxy-(C$_1$-C$_6$-alkyl-)), —NH((C$_1$-C$_6$-alkyl)amino-(C$_1$-C$_6$-alkyl-)), —NH(di-(C$_1$-C$_6$-alkyl)amino-(C$_1$-C$_6$-alkyl-)), —NH(heterocyclyl-(C$_1$-C$_6$-alkyl-)), —NH(heteroaryl-(C$_1$-C$_6$-alkyl-)), —NH(phenyl-(C$_1$-C$_6$-alkyl-)), —C(O)NH$_2$, —C(O)NH—(C$_1$-C$_6$-alkyl), —C(O)N(C$_1$-C$_6$-alkyl)$_2$, —C(O)NH(C$_1$-C$_6$-alkyl), —C(O)NH(amino-(C$_1$-C$_6$-alkyl-)), —C(O)NH(hydroxy-(C$_1$-C$_6$-alkyl-)), —C(O)NH((C$_1$-C$_6$-alkyl)amino-(C$_1$-C$_6$-alkyl-)), —C(O)NH(di-(C$_1$-C$_6$-alkyl)amino-(C$_1$-C$_6$-alkyl-)), —C(O)NH(heterocyclyl-(C$_1$-C$_6$-alkyl-)), —C(O)NH (heteroaryl-(C$_1$-C$_6$-alkyl-)), —C(O)NH(phenyl-(C$_1$-C$_6$-alkyl-)), heterocyclyl, trifluoromethyl and trifluoromethoxy, and heteroaryl, heterocyclyl and phenyl may in turn be at least monosubstituted by C$_1$-C$_6$-alkyl, C$_1$-C$_6$-alkoxy, halogen, trifluoromethyl, trifluoromethoxy or OH;

$R^4$ is particularly preferably selected from the group consisting of:

hydrogen, fluorine, chlorine, bromine, —CN, —C(O)NH (2-cyclohexylaminoethyl-), —C(O)NH(3-(4-methylpiperazin-1-yl)propyl-), —C(O)NH(3-hydroxypropyl-), —C(O)NH(3-cyclohexylaminopropyl-), methyl, ethyl and trifluoromethyl;

$R^5$ is preferably selected from the group consisting of:

hydrogen, halogen, —CN, —CH$_2$—R$^8$, —OR$^8$, —C(O)R$^8$, —C(O)OR$^8$, —NR$^8$H, —NR$^8$(C$_1$-C$_6$-alkyl-), —C(O)NR$^8$H, —SR$^8$, —SO$_2$NR$^8$H, —SO$_2$—R$^8$, aryl, heteroaryl, heterocyclyl, trifluoromethyl and trifluoromethoxy, and heterocyclyl, aryl and heteroaryl may in turn be at least monosubstituted by C$_1$-C$_6$-alkyl, C$_1$-C$_6$-alkoxy, oxo, halogen, trifluoromethyl, trifluoromethoxy or OH;

$R^5$ is more preferably selected from the group consisting of:

hydrogen, fluorine, chlorine, bromine, —CN, —CH$_2$—R$^8$, —OR$^8$, —C(O)R$^8$, —C(O)OR$^8$, —NR$^8$H, —NR$^8$(C$_1$-C$_6$-alkyl-), —C(O)NR$^8$H, —SR$^8$, —SO$_2$NR$^8$H, —SO$_2$—R$^8$, heterocyclyl, trifluoromethyl and trifluoromethoxy, and heterocyclyl may in turn be at least monosubstituted by C$_1$-C$_6$-alkyl, C$_1$-C$_6$-alkoxy, halogen, trifluoromethyl, trifluoromethoxy or OH;

$R^5$ is much more preferably selected from the group consisting of:

hydrogen, fluorine, chlorine, bromine, —CN, C$_1$-C$_6$-alkyl, phenyl-(C$_1$-C$_6$-alkyl)-, —OH, C$_1$-C$_6$-alkoxy, —O-phenyl, —C(O)OH, —C(O)O—(C$_1$-C$_6$-alkyl), —NR$^8$H, —NR$^8$(C$_1$-C$_6$-alkyl-), —C(O)NR$^8$H, heterocyclyl, trifluoromethyl and trifluoromethoxy, and heterocyclyl and phenyl may in turn be at least monosubstituted by C$_1$-C$_6$-alkyl, C$_1$-C$_6$-alkoxy, halogen, trifluoromethyl, trifluoromethoxy or OH;

$R^5$ is even much more preferably selected from the group consisting of:

hydrogen, fluorine, chlorine, bromine, —CN, C$_1$-C$_6$-alkyl, —OH, C$_1$-C$_6$-alkoxy, —C(O)OH, —C(O)O—(C$_1$-C$_6$-alkyl), —NH$_2$, —N(C$_1$-C$_6$-alkyl)$_2$, —NH(C$_1$-C$_6$-alkyl), —NH(amino-(C$_1$-C$_6$-alkyl-)), —NH(hydroxy-(C$_1$-C$_6$-alkyl-)), —NH((C$_1$-C$_6$-alkyl)amino-(C$_1$-C$_6$-alkyl-)), —NH(di-(C$_1$-C$_6$-alkyl)amino-(C$_1$-C$_6$-alkyl-)), —NH(heterocyclyl-(C$_1$-C$_6$-alkyl-)), —NH(heteroaryl-(C$_1$-C$_6$-alkyl-)), —NH(phenyl-(C$_1$-C$_6$-alkyl-)), —C(O)NH$_2$, —C(O)NH—(C$_1$-C$_6$-alkyl), —C(O)N(C$_1$-C$_6$-alkyl)$_2$, —C(O)NH(C$_1$-C$_6$-alkyl), —C(O)NH(amino-(C$_1$-C$_6$-alkyl-)), —C(O)NH(hydroxy-(C$_1$-C$_6$-alkyl-)), —C(O)NH((C$_1$-C$_6$-alkyl)amino-(C$_1$-C$_6$-alkyl-)), —C(O)NH(di-(C$_1$-C$_6$-alkyl)amino-(C$_1$-C$_6$-alkyl-)), —C(O)NH(heterocyclyl-(C$_1$-C$_6$-alkyl-)), —C(O)NH (heteroaryl-(C$_1$-C$_6$-alkyl-)), —C(O)NH(phenyl-(C$_1$-C$_6$-alkyl-)), heterocyclyl, trifluoromethyl and trifluoromethoxy, and heteroaryl, heterocyclyl and phenyl may in turn be at least monosubstituted by C$_1$-C$_6$-alkyl, C$_1$-C$_6$-alkoxy, halogen, trifluoromethyl, trifluoromethoxy or OH;

$R^5$ is particularly preferably selected from the group consisting of:

hydrogen, fluorine, chlorine, bromine, —CN, —C(O)NH (2-cyclohexylamino-ethyl-), —C(O)NH(3-(4-methylpiperazin-1-yl)propyl-), —C(O)NH(3-hydroxypropyl-), —C(O)NH(3-cyclohexylaminopropyl-), methyl, ethyl and trifluoromethyl;

$R^6$ is preferably selected from the group consisting of:
hydrogen, halogen, —CN, —CH$_2$—$R^8$, —O$R^8$, —C(O)$R^8$, —C(O)O$R^8$, —N$R^8$H, —N$R^8$(C$_1$-C$_6$-alkyl-), —C(O)N$R^8$H, —S$R^8$, —SO$_2$N$R^8$H, —SO$_2$—$R^8$, aryl, heteroaryl, heterocyclyl, trifluoromethyl and trifluoromethoxy,
and heterocyclyl, aryl and heteroaryl may in turn be at least monosubstituted by C$_1$-C$_6$-alkyl, C$_1$-C$_6$-alkoxy, oxo, halogen, trifluoromethyl, trifluoromethoxy or OH;

$R^6$ is more preferably selected from the group consisting of:
hydrogen, fluorine, chlorine, bromine, —CN, —CH$_2$—$R^8$, —O$R^8$, —C(O)$R^8$, —C(O)O$R^8$, —N$R^8$H, —N$R^8$(C$_1$-C$_6$-alkyl-), —C(O)N$R^8$H, —S$R^8$, —SO$_2$N$R^8$H, —SO$_2$—$R^8$, heterocyclyl, trifluoromethyl and trifluoromethoxy,
and heterocyclyl may in turn be at least monosubstituted by C$_1$-C$_6$-alkyl, C$_1$-C$_6$-alkoxy, halogen, trifluoromethyl, trifluoromethoxy or OH;

$R^6$ is much more preferably selected from the group consisting of:
hydrogen, fluorine, chlorine, bromine, —CN, C$_1$-C$_6$-alkyl, phenyl-(C$_1$-C$_6$-alkyl)-, —OH, C$_1$-C$_6$-alkoxy, —O-phenyl, —C(O)OH, —C(O)O—(C$_1$-C$_6$-alkyl), —N$R^8$H, —N$R^8$(C$_1$-C$_6$-alkyl-), —C(O)N$R^8$H, heterocyclyl, trifluoromethyl and trifluoromethoxy,
and heterocyclyl and phenyl may in turn be at least monosubstituted by C$_1$-C$_6$-alkyl, C$_1$-C$_6$-alkoxy, halogen, trifluoromethyl, trifluoromethoxy or OH;

$R^6$ is even much more preferably selected from the group consisting of:
hydrogen, fluorine, chlorine, bromine, —CN, C$_1$-C$_6$-alkyl, —OH, C$_1$-C$_6$-alkoxy, —C(O)OH, —C(O)O—(C$_1$-C$_6$-alkyl), —NH$_2$, —N(C$_1$-C$_6$-alkyl)$_2$, —NH(C$_1$-C$_6$-alkyl), —NH(amino-(C$_1$-C$_6$-alkyl-)), —NH(hydroxy-(C$_1$-C$_6$-alkyl-)), —NH((C$_1$-C$_6$-alkyl)amino-(C$_1$-C$_6$-alkyl-)), —NH(di-(C$_1$-C$_6$-alkyl)amino-(C$_1$-C$_6$-alkyl-)), —NH(heterocyclyl-(C$_1$-C$_6$-alkyl-)), —NH(heteroaryl-(C$_1$-C$_6$-alkyl-)), —NH(phenyl-(C$_1$-C$_6$-alkyl-)), —C(O)NH$_2$, —C(O)NH—(C$_1$-C$_6$-alkyl), —C(O)N(C$_1$-C$_6$-alkyl)$_2$, —C(O)NH(C$_1$-C$_6$-alkyl), —C(O)NH(amino-(C$_1$-C$_6$-alkyl-)), —C(O)NH(hydroxy-(C$_1$-C$_6$-alkyl-)), —C(O)NH((C$_1$-C$_6$-alkyl)amino-(C$_1$-C$_6$-alkyl-)), —C(O)NH(di-(C$_1$-C$_6$alkyl-)), -alkyl)amino-(C$_1$-C$_6$—C(O)NH(heterocyclyl-(C$_1$-C$_6$-alkyl-)), —C(O)NH(heteroaryl-(C$_1$-C$_6$-alkyl-)), —C(O)NH(phenyl-(C$_1$-C$_6$-alkyl-)), heterocyclyl, trifluoromethyl and trifluoromethoxy,
and heteroaryl, heterocyclyl and phenyl may in turn be at least monosubstituted by C$_1$-C$_6$-alkyl, C$_1$-C$_6$-alkoxy, halogen, trifluoromethyl, trifluoromethoxy or OH;

$R^6$ is particularly preferably selected from the group consisting of:
hydrogen, fluorine, chlorine, bromine, —CN, —C(O)NH(2-cyclohexylamino-ethyl-), —C(O)NH(3-(4-methylpiperazin-1-yl)propyl-), —C(O)NH(3-hydroxy-propyl-), —C(O)NH(3-cyclohexylaminopropyl-), methyl, ethyl and trifluoromethyl;

$R^6$ is very particularly preferably hydrogen;

$R^7$ is preferably:
H;
unsubstituted or at least monosubstituted C$_1$-C$_6$-alkyl, heterocyclyl, phenyl or heteroaryl,
where the substituents are selected from the group consisting of: heteroaryl, heterocyclyl, phenyl, fluorine, chlorine, bromine, OH, C$_1$-C$_6$-alkoxy, trifluoromethyl, trifluoromethoxy, NH$_2$, (C$_1$-C$_6$-alkyl)amino- and di-(C$_1$-C$_6$-alkyl)amino-,
and heterocyclyl, phenyl and heteroaryl may in turn be at least monosubstituted by C$_1$-C$_3$-alkyl, C$_1$-C$_3$-alkoxy, oxo, trifluoromethyl, trifluoromethoxy, fluorine, chlorine or OH;

$R^7$ is more preferably:
unsubstituted or at least monosubstituted C$_1$-C$_6$-alkyl,
where the substituents are selected from the group consisting of: heteroaryl, heterocyclyl, OH, NH$_2$, (C$_1$-C$_6$-alkyl)amino- and di-(C$_1$-C$_6$-alkyl)amino-,
and heterocyclyl, and heteroaryl may in turn be at least monosubstituted by C$_1$-C$_3$-alkyl, C$_1$-C$_3$-alkoxy, trifluoromethyl, trifluoromethoxy, fluorine, chlorine or OH;

$R^7$ is particularly preferably:
unsubstituted or at least monosubstituted C$_1$-C$_4$-alkyl,
where the substituents are selected from the group consisting of: morpholinyl, piperazinyl, piperidinyl, pyridinyl, imidazolyl, pyrimidinyl, NH$_2$, (C$_1$-C$_6$-alkyl)amino- and di-(C$_1$-C$_6$-alkyl)amino-,
and morpholinyl, piperazinyl, piperidinyl, pyridinyl, imidazolyl and pyrimidinyl may in turn be monosubstituted by C$_1$-C$_3$-alkyl, C$_1$-C$_3$-alkoxy, trifluoromethyl, trifluoromethoxy, fluorine, chlorine or OH;

$R^8$ is preferably:
H;
unsubstituted or at least monosubstituted C$_1$-C$_6$-alkyl, heterocyclyl, phenyl or heteroaryl,
where the substituents are selected from the group consisting of: heteroaryl, heterocyclyl, phenyl, fluorine, chlorine, bromine, OH, C$_1$-C$_6$-alkoxy, trifluoromethyl, trifluoromethoxy, NH$_2$, (C$_1$-C$_6$-alkyl)amino- and di-(C$_1$-C$_6$-alkyl)amino-,
and heterocyclyl, phenyl and heteroaryl may in turn be at least monosubstituted by C$_1$-C$_3$-alkyl, C$_1$-C$_3$-alkoxy, oxo, trifluoromethyl, trifluoromethoxy, fluorine, chlorine or OH;

$R^8$ is more preferably:
unsubstituted or at least monosubstituted C$_1$-C$_6$-alkyl,
where the substituents are selected from the group consisting of: heteroaryl, heterocyclyl, OH, NH$_2$, (C$_1$-C$_6$-alkyl)amino- and di-(C$_1$-C$_6$-alkyl)amino-,
and heterocyclyl, and heteroaryl may in turn be at least monosubstituted by C$_1$-C$_3$-alkyl, C$_1$-C$_3$-alkoxy, trifluoromethyl, trifluoromethoxy, fluorine, chlorine or OH;

$R^8$ is particularly preferably:
unsubstituted or at least monosubstituted C$_1$-C$_4$-alkyl,
where the substituents are selected from the group consisting of: morpholinyl, piperazinyl, piperidinyl, pyridinyl, imidazolyl, pyrimidinyl, NH$_2$, (C$_1$-C$_6$-alkyl)amino- and di-(C$_1$-C$_6$-alkyl)amino-,
and morpholinyl, piperazinyl, piperidinyl, pyridinyl, imidazolyl and pyrimidinyl may in turn be monosubstituted by C$_1$-C$_3$-alkyl, C$_1$-C$_3$-alkoxy, trifluoromethyl, trifluoromethoxy, fluorine, chlorine or OH;

Heteroaryl is preferably imidazolyl, thiophenyl, furanyl, oxazolyl, isoxazolyl, pyridinyl, pyrimidinyl, pyrazolyl, benzo[b]thiophenyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzodioxolyl; heteroaryl is particularly preferably pyridinyl, thiophenyl or pyrimidinyl;

Aryl is preferably naphthyl, indanyl or phenyl; Aryl is particularly preferably phenyl.

Heterocyclyl is preferably 2-oxo-azepanyl, tetrahydrofuranyl, 1,3-dioxolanyl, morpholinyl, pyrrolidinyl, piperazinyl or piperidinyl; heterocyclyl is particularly preferably piperidinyl, morpholinyl or piperazinyl;

Examples of embodiments with preferred compounds of the general formula (I) with reference to the meanings (definitions) described above are:

i) $R^1$, $R^2$, $R^3$, $R^4$, $R^5$, $R^6$, $R^7$, $R^8$, A, B, D, E, heteroaryl, heterocyclyl and aryl have their preferred meaning; or
ii) $R^1$ has its preferred meaning and all other substituents have their basic meaning; or
iii) $R^2$ has its preferred meaning and all other substituents have their basic meaning; or
iv) $R^3$ has its preferred meaning and all other substituents have their basic meaning; or
v) $R^4$ has its preferred meaning and all other substituents have their basic meaning; or
vi) $R^5$ has its preferred meaning and all other substituents have their basic meaning; or
vii) $R^6$ has its preferred meaning and all other substituents have their basic meaning; or
viii) $R^7$ has its preferred meaning and all other substituents have their basic meaning; or
ix) $R^8$ has its preferred meaning and all other substituents have their basic meaning; or
x) A has its preferred meaning and all other substituents have their basic meaning; or
xi) B has its preferred meaning and all other substituents have their basic meaning; or
xii) D has its preferred meaning and all other substituents have their basic meaning; or
xiii) E has its preferred meaning and all other substituents have their basic meaning; or
xiv) heteroaryl has its preferred meaning and all other substituents have their basic meaning; or
xv) heterocyclyl has its preferred meaning and all other substituents have their basic meaning; or
xvi) aryl has its preferred meaning and all other substituents have their basic meaning; or
xvii) $R^1$, $R^2$, $R^3$, $R^4$, $R^5$, $R^6$, $R^7$, $R^8$, A, E, heteroaryl, heterocyclyl and aryl have their preferred meaning and B and D have their basic meaning; or
xviii) $R^1$, $R^3$, $R^4$, $R^5$ and $R^6$ have their more preferred meaning, $R^7$, $R^8$, A, D, E, heteroaryl, heterocyclyl and aryl have their preferred meaning, $R^2$ has its particularly preferred meaning and B has its basic meaning; or
xix) $R^1$ has its much more preferred meaning, $R^3$, $R^4$, $R^5$ and $R^6$ have their even much more preferred meaning, A, D, E, heteroaryl and heterocyclyl have their preferred meaning, $R^2$ has its particularly preferred meaning and B has its basic meaning; or
xx) $R^1$ has its very particularly preferred meaning, $R^2$, $R^3$, $R^4$, $R^5$ and $R^6$ have their particularly preferred meaning, A, D and E have their preferred meaning, and B has its basic meaning; or
xxi) $R^1$, $R^3$ and $R^6$ have their very particularly preferred meaning, $R^2$, $R^4$ and $R^5$ have their particularly preferred meaning, A, D and E have their preferred meaning, and B has its basic meaning; or
xxii) $R^3$ and $R^6$ have their very particularly preferred meaning, $R^1$, $R^2$, $R^4$ and $R^5$ have their particularly preferred meaning, A, D and E have their preferred meaning, and B has its basic meaning; or
xxiii) $R^1$, $R^2$, $R^3$, $R^4$, $R^5$ and $R^6$ have their particularly preferred meaning, A, D and E have their preferred meaning, and B has its basic meaning; or
xxiv) $R^1$ has its much more preferred meaning, $R^2$, $R^3$, $R^4$, $R^5$ and $R^6$ have their particularly preferred meaning, A, D, E, heteroaryl and heterocyclyl have their preferred meaning and B has its basic meaning; or
xxv) $R^1$ has its much more preferred meaning, $R^3$ and $R^6$ have their very particularly preferred meaning, $R^2$, $R^4$ and $R^5$ have their particularly preferred meaning, A, D, E, heteroaryl and heterocyclyl have their preferred meaning and B has its basic meaning; or
xxvi) $R^1$ has its much more preferred meaning, $R^3$ and $R^6$ have their very particularly preferred meaning, $R^2$, $R^4$, $R^5$, heteroaryl and heterocyclyl have their particularly preferred meaning, A, D and E have their preferred meaning and B has its basic meaning; or
xxvii) $R^1$ has its much more preferred meaning, $R^2$, $R^3$, $R^4$, $R^5$, $R^6$, heteroaryl and heterocyclyl have their particularly preferred meaning, A, D and E have their preferred meaning and B has its basic meaning; or
xxviii) $R^1$ has its much more preferred meaning, $R^3$, $R^4$, $R^5$, $R^6$, heteroaryl and heterocyclyl have their particularly preferred meaning, $R^2$, A, D and E have their preferred meaning and B has its basic meaning; or
xxix) $R^1$, $R^4$, $R^5$, $R^7$, $R^8$, A, E, heteroaryl, heterocyclyl and aryl have their preferred meaning, $R^3$ and $R^6$ have their very particularly preferred meaning, $R^2$ has its particularly preferred meaning and B and D have their basic meaning; or
xxx) $R^1$, $R^3$, $R^4$, $R^5$, $R^6$, A, E, heteroaryl, heterocyclyl and aryl have their preferred meaning, $R^7$ and $R^8$ have their more preferred meaning, $R^2$ has its particularly preferred meaning and B and D have their basic meaning; or
xxxi) $R^1$, $R^3$, $R^4$, $R^5$, $R^6$ have their more preferred meaning, $R^2$, A, D, E, heteroaryl, heterocyclyl and aryl have their preferred meaning, $R^7$ and $R^8$ have their particularly preferred meaning and B has its basic meaning; or
xxxii) $R^1$, $R^3$, $R^4$, $R^5$, $R^6$ have their more preferred meaning, A, D, E, heteroaryl, heterocyclyl and aryl have their preferred meaning, $R^2$, $R^7$ and $R^8$ have their particularly preferred meaning and B and D have their basic meaning; or
xxxiii) $R^1$ has its more preferred meaning, $R^7$, A, D, E, heteroaryl, heterocyclyl and aryl have their preferred meaning, $R^4$ and $R^5$ have their even much more preferred meaning, $R^3$ and $R^6$ have their very particularly preferred meaning, $R^2$ has its particularly preferred meaning and B and D have their basic meaning; or
xxxiv) $R^1$ has its much more preferred meaning, $R^3$, $R^4$, $R^5$ and $R^6$ have their more preferred meaning, $R^8$, A, D, E, heteroaryl, heterocyclyl and aryl have their preferred meaning, $R^2$ has its particularly preferred meaning and B has its basic meaning;

As stated above, the preferred compounds of the general formula (I) are not confined to the aforementioned examples. On the contrary, all combinations of the individual substituents in their basic meaning with the preferred, more preferred, even more preferred, much more preferred, even much more preferred, particularly preferred or very particularly preferred meanings of the other substituents or all combinations of the preferred, more preferred, even more preferred, much more preferred, even much more preferred, particularly preferred or very particularly preferred meanings of the individual substituents possible which are not mentioned above as example are also an aspect of this invention. This only applies, of course, to the extent that the definitions of the respective substituents permits such a combination.

Particularly preferred compounds of the general formula (I) are selected from the group consisting of: 4-(6-trifluoromethyl-1H-benzimidazol-2-yl)-6-pyridin-4-yl-2H-pyridazin-3-one, 4-(5-chloro-1H-benzimidazol-2-yl)-6-(2-methylamino-pyrimidin-4-yl)-2H-pyridazin-3-one, 4-(6-chloro- 1H-benzimidazol-2-yl)-6-(4-hydroxy-3-methoxy-phenyl)-2H-pyridazin-3-one, 4-(5-fluoro-1H-benzimidazol-2-yl)-6-pyridin-4one, -yl-2H-pyridazin-3-6-(2-butylamino-pyrimidin-4-yl)-4-(6-chloro-1H-benzimidazol-2-yl) -2H-pyridazin-3-one, 4-(1H-benzimidazol-2-yl)-6-pyridin-4-yl-2H-pyridazin-3-one, 4-(6-chloro- 1H-benzimidazol-2-yl)-6-[2-((R)-1-phenyl-ethylamino)-pyrimidin-4-yl]-2H-pyridazin-3-one, 4-(5,6-dichloro-1H-benzimidazol-2-yl)-6-pyridin-4-yl-2H-pyridazin-3-one, 6-[2-(2-morpholin-4-yl-ethylamino)-pyrimidin-4-yl]-4-(6-trifluoromethyl-1H-benzimidazol-2-yl)-2H-pyridazin-3-one and 4-(3H-imidazol[4,5-c]pyridin-2-yl)-6-pyridin-4-yl-2H-pyridazin-3-one.

It is expressly pointed out once again that the above statements concerning the salts, stereoisomers, prodrugs, N-oxides etc. apply also to the preferred and particularly preferred compounds of formula (I); in particular, the respective physiologically tolerated salts are also included.

The compounds are prepared according to processes known per se by preparing the monoacyl derivatives (IV) from active acid derivatives of the formula (II), where Y is a leaving group, preferably —OH, $C_1$-$C_{10}$-alkoxy, chlorine, —O—C(O)—($C_1$-$C_{10}$-alkyl or —O—C(O)—O—($C_1$-$C_{10}$-alkyl), and 1,2-diaminophenyl or 1,2-diaminoheterocyclyl derivatives of the formula (III), and cyclizing the monoacyl derivatives in a suitable manner. Suitable cyclizing agents may be acids such as glacial acetic acid, hydrochloric acid, sulfuric acid, phosphoric acid or dehydrating agents such as phosphorus pentoxide. After the cyclization, the substituents A, B, D, E, $R^1$ and $R^2$ (and the other substituents) can where appropriate be modified by known processes to give the claimed compounds of the formula (I).

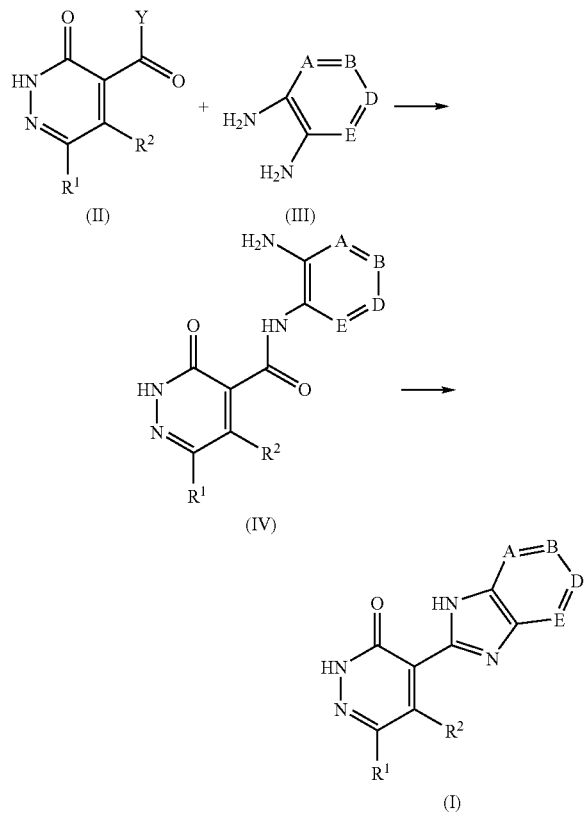

A further known preparation method consists of reacting aldehyde, i.e. Y in formula (II) equals hydrogen, with the compounds of the formula (III), in which case the initially formed dihydro compounds are converted by air or (pure) oxygen or other oxidants into the compounds of the formula (I).

A further possibility is to prepare the compounds of the general formula (I) by palladium-catalyzed coupling in a Suzuki reaction (I. Parrot et al., Synthesis; 7; 1999; 1163 to 1168). In this case, a compound of the formula (VI), where Y1 equals halogen, B(OH)$_2$ or Sn($C_1$-$C_{10}$-alkyl) and Y2 equals H or a protective group, is reacted with a compound of the formula (V).

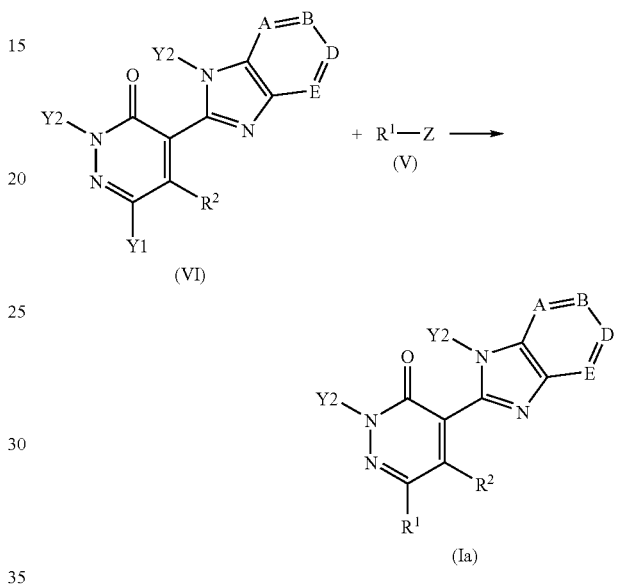

$R^1$ in formula (V) equals unsubstituted or at least monosubstituted aryl or heteroaryl as defined for formula (I). Z can be, for example, B(OH)$_2$, B($C_1$-$C_{10}$-alkyl)$_2$, Sn—($C_1$-$C_{10}$-alkyl)$_3$, Zn—($C_1$-$C_{10}$-alkyl) or halogen. Where Y2 is a protective group, the latter is removed again by methods known to the skilled worker following the reaction of (VI) with (V). All protective groups known to the skilled worker can be used as protective group, preferably trimethylsilylethoxymethyl-. All palladium complexes known to the skilled worker are suitable for carrying out the palladium-catalyzed coupling, with preference for the use of Pd(triphenylphosphine)$_4$ (Pd-tetrakis catalyst), which is preferably formed in situ from palladium acetate. Formula (Ia) corresponds to formula (I) for Y2=H and $R^1$ equal to unsubstituted or at least monosubstituted aryl or heteroaryl.

All synthetic reactions for compounds of the formula (I) are known in principle to the skilled worker and can accordingly be carried out under standard conditions (identical or with slight modifications) as described in the literature (see, for example, in Houben-Weyl, Methoden der organischen Chemie, Thieme-Verlag, Stuttgart or Organic Reactions, John Wiley & Sons, New York). Based on the circumstances in the individual case, it may, in order to avoid side reactions during the preparation for compounds of formula (I), be necessary or advantageous to block functional groups temporarily through the introduction of protective groups, and to remove them again later. It is also possible where appropriate for functional groups to be introduced in the form of precursor groups, in which case the latter are converted in a later reaction step into the desired functional group. Such synthetic strategies, protective groups and precursor groups suitable for the individual case are known to the skilled worker. Where necessary, the compounds of formula (I) can be purified by known workup methods, for example by recrystallization or chromatography. The starting materials for preparing compounds of formula (I) are either commercially available or they can be prepared by processes known from the literature. Compounds and intermediates prepared by the synthetic processes described above are a further aspect of the present invention.

The present invention also relates to the use of compounds of the general formula (I) as pharmaceutical or medicament. Concerning the definition of the substituents A, B, D, E, $R^1$ and $R^2$ (and the other substituents defined via the aforementioned substituents), reference is made to the statements concerning the compounds as such.

The use of compounds of the general formula (I) as pharmaceuticals, where one, more than one or all of the aforementioned substituents have the abovementioned preferred, more preferred, even more preferred, much more preferred, even much more preferred, particularly preferred or very particularly preferred meaning, including all combinations with one another, is likewise an aspect of the present invention.

The compounds of general formula (I) are kinase inhibitors and can therefore be employed for the treatment of diseases, which may result from an abnormal activity of kinases. As abnormal kinase activity, there may be mentioned, for example, that of CDK2 and the like.

In particular, compounds according to the present invention can be used for the inhibition of the kinase CDK2. Since CDK2 is usually part of a complex, such as CDK2/cyclin A or CDK2/cyclin E complexes, the compounds of the present invention can also be used as inhibitors of CDK2/cyclin A or CDK2/cyclin E. This effect is particularly relevant for the treatment of neoplastic diseases such as cancer.

Examples of diseases, which can be treated with the compounds according to the present invention, include: neoplastic diseases, preferably cancer, in particular a solid tumor or leukemia.

Within the present invention a solid tumor is defined as a tumor, which does not affect the hematopoietic or lymphatic system. An example of a solid tumor is an epithelial tumor.

In the above statements the term treatment also includes prophylaxis, therapy or curing of the abovementioned diseases.

All references to "compound(s) according to formula (I)" refer hereinbelow to a compound/compounds of the formula (I) as described above and also to their salts, solvates and physiologically functional derivatives as described herein.

The compounds of the formula (I) can be administered to animals and humans, preferably to mammals and humans, and in particular to humans. The compounds of the formula (I) can be administered as pharmaceuticals by themselves, in mixtures with one another or in mixtures with other pharmaceuticals or in the form of pharmaceutical preparations. Further subjects of the present invention therefore also are the use of the compounds of the formula (I) for preparing one or more medicaments for prophylaxis and/or treatment of the abovementioned diseases, pharmaceutical preparations (or pharmaceutical compositions) comprising an effective dose of at least one compound of the formula (I) as well as pharmaceutical preparations comprising an effective dose of at least one compound of the formula (I) for prophylaxis and/or treatment of the abovementioned diseases.

The amount of a compound according to formula (I) which is required in order to attain the desired biological effect depends on a number of factors, for example the specific compound selected, the intended use, the type of administration and the clinical state of the patient. In general, the daily dose is in the range from 0.3 mg to 100 mg (typically from 3 mg to 50 mg) per day per kilogram of body weight, for example 3-10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampoules for injections can contain, for example, from 1 mg to 100 mg, and orally administerable individual dose formulations such as, for example, tablets or capsules can contain, for example, from 1.0 to 1000 mg, typically from 10 to 600 mg. In the case of pharmaceutically acceptable salts, the abovementioned masses relate to the mass of the free compound on which the salt is based. The compound used for the prophylaxis or therapy of the abovementioned conditions may be the compounds according to formula (I) themselves, but they are preferably present in the form of a pharmaceutical composition together with an acceptable carrier. The carrier must be naturally acceptable, in the sense that it is compatible with the other ingredients of said composition and is not harmful to the patient's health (physiologically tolerable). The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The pharmaceutical compositions of the invention may be prepared according to any of the known pharmaceutical methods which essentially comprise mixing the ingredients with pharmacologically acceptable carriers and/or excipients.

Besides at least one compound according to formula (i) as well as one or more carriers, the pharmaceutical preparations according to the invention can also contain additives. As additives can be employed, for example: fillers, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants. The pharmaceutical compositions of the invention may be in the form of a pill, tablet, coated tablet, lozenge, granule, capsule, hard or soft gelatin capsule, aqueous solution, alcoholic solution, oily solution, syrup, emulsion, suspension, suppository, pastille, solution for injection or infusion, ointment, tincture, cream, lotion, powder, spray, transdermal therapeutic systems, nasal spray, aerosol, aerosol mixture, microcapsule, implant, rod or patch.

Pharmaceutical compositions of the invention are those which are suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. Preference is given to acid-resistant and enteric formulations. Suitable enteric coatings include cellulose acetate phthalate, polyvinyl acetate phthalate, hydroxypropyl-methylcellulose phthalate and anionic polymers of methacrylic acid and methyl methacrylate.

Suitable pharmaceutical compounds for oral administration may be present in separate units such as, for example, capsules, cachets, lozenges or tablets, which in each case contain a particular amount of the compound according to formula (I); as powders (gelatin capsules or cachets) or granules; as solution or suspension in an aqueous or nonaqueous liquid; or as an oil-in-water or water-in-oil emulsion. As already mentioned, said compositions can be prepared according to any suitable pharmaceutical method which includes a step in which the active compound and the carrier (which may comprise one or more additional components) are contacted. In general, the compositions are prepared by uniform and homogeneous mixing of the active compound with a liquid and/or finely dispersed solid carrier, after which the product is shaped, if necessary. Thus a tablet, for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine. As diluents can be used, for example, starch, cellulose, sucrose, lactose or silica. The pharmaceutical compositions of the invention may also comprise substances other than diluents, for example one or more lubricants such as magnesium stearate or talc, a coloring, a coating (sugar-coated tablets) or a varnish.

Pharmaceutical compositions which are suitable for peroral (sublingual) administration include lozenges which contain a compound according to formula (I) with a flavoring, usually sucrose and gum arabic or tragacanth, and pastilles which comprise the compound in an inert base such as gelatin and glycerol or sucrose and gum arabic.

Suitable pharmaceutical compositions for parenteral administration preferably comprise sterile aqueous preparations of a compound according to formula (I) which are preferably isotonic with the blood of the intended recipient. These preparations are preferably administered intravenously, although they may also be administered subcutaneously, intramuscularly or intradermally as an injection. Said preparations may preferably be prepared by mixing the compound with water and rendering the obtained solution sterile and isotonic with the blood. Injectable compositions of the invention generally contain from 0.1 to 5% by weight of the active compound.

These sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, organic esters for injection, for example ethyl oleate or other suitable organic solvents. These compositions may also contain adjuvants, in particular wetting, isotonicizing, emulsifying, dispersing and stabilizing media. The sterilization may be carried out in several ways, for example by an aseptic filtration, by incorporating sterilizing agents into the composition, by irradiation or by heating. They may also be prepared in the form of sterile solid compositions which may be dissolved at the time of use in sterile water or in any other sterile medium for injection.

Suitable pharmaceutical compositions for rectal administration are preferably present as individual dose suppositories. These may be prepared by mixing a compound according to formula (I) with one or more conventional solid carriers, for example cocoa butter, and shaping the resulting mixture.

Suitable pharmaceutical compositions for topical application to the skin are preferably present as ointment, cream, lotion, paste, spray, aerosol or oil. Carriers which may be used are petroleum jelly, lanolin, polyethylene glycols, alcohols and combinations of two or more of these substances. In general, the active compound is present at a concentration of from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 1% to 35%, preferably approx. 3% to 15%. A particular possibility is the release of the active compound by electro-transport or iontophoresis, as described, for example, in Pharmaceutical Research, 2(6): 318 (1986).

The following examples illustrate the pharmaceutical compositions according to the invention:

EXAMPLE A

Gelatin capsules containing a dose of 50 mg of active compound and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Gelatin capsules containing a dose of 50 mg of active compound and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs 1 finished film-coated tablet of 245 mg | |

EXAMPLE C

A solution for injection containing 10 mg of active compound and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol at 95% | 0.4 ml |
| Sodium hydroxide | 24 mg |
| Propylene glycol | 1.6 ml |
| Water | qs 4 ml |

Another aspect of the present invention is the combination of compounds of the formula (I) with other pharmaceutically active substances not covered by formula (I).

The compounds of the present invention may be administered alone or mixed with other anticancer agents. Among the possible combinations, there may be mentioned:

alkylating agents and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine;

platinum derivatives such as in particular cisplatin, carboplatin or oxaliplatin;

antibiotic agents such as in particular bleomycin, mitomycin or dactinomycin;

antimicrotubule agents such as in particular vinblastine, vincristine, vindesine, vinorelbine or taxoids (paclitaxel and docetaxel);

anthracyclines such as in particular doxorubicin, daunorubicin, idarubicin, epirubicin, mitoxantrone or losoxantrone;

group I and II topoisomerases such as etoposide, teniposide, amsacrine, irinotecan, topotecan or tomudex;

fluoropyrimidines such as 5-fluorouracil, UFT or floxuridine;

cytidine analogues such as 5-azacytidine, cytarabine, gemcitabine, 6-mercaptomurine or 6-thioguanine;

adenosine analogues such as pentostatin, cytarabine or fludarabine phosphate;

methotrexate and folinic acid;

various enzymes and compounds such as L-asparaginase, hydroxyurea, trans-retinoic acid, suramine, dexrazoxane, amifostine, herceptin as well as oestrogenic and androgenic hormones.

It is also possible to combine a radiation treatment with the compounds of the present invention. This treatment may be administered simultaneously, separately or sequentially. The treatment will be adapted to the patient to be treated by the practitioner.

The following examples illustrate the invention without limitation.

EXAMPLE 1

Methyl 2-(3-oxo-6-pyridin-4-yl-2,3-dihydropyridazin-4-yl)-1H-benzimidazole-5-carboxylate

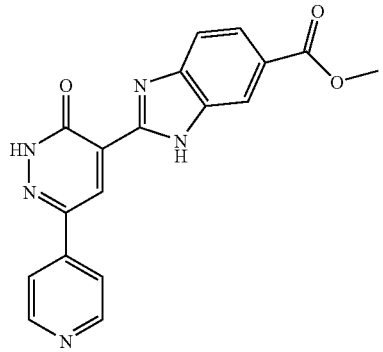

a) Methyl 4-amino-3-[(3-oxo-6-pyridin-4-yl-2,3-dihydropyridazine-4-carbonyl)-amino]benzoate A mixture consisting of 2.1 g of 3-oxo-6-pyridin-4-yl-2,3-dihydropyridazine-4-carboxylic acid, 4 ml of thionyl chloride and 20 ml of dimethoxyethane is stirred at 100° C. for 5 hours and then evaporated to dryness in vacuo. The residue is suspended in 20 ml of dimethoxyethane, mixed with 3 g of triethylamine and 1.7 g of methyl 3,4-diaminobenzoate and stirred at room temperature overnight. The volatile constituents are stripped off in vacuo, and the residue is stirred with 10 ml of saturated sodium bicarbonate solution and filtered off with suction.

Yield: 1.3 g m.p.: 352° C.

b) Methyl 2-(3-oxo-6-pyridin-4-yl-2,3-dihydro-pyridazin-4-yl)-1H-benzimidazole-5-carboxylate A mixture of 1.3 g of methyl 4-amino-3-[(3-oxo-6-pyridin-4-yl-2,3-dihydro-pyridazine-4-carbonyl)amino]benzoate and 20 ml of glacial acetic acid is heated with stirring at 100° C. for 10 hours. The precipitate which has formed is filtered off with suction, washed with water and dried in vacuo at 50° C.

Yield: 1.07 g m.p.: >300° C. (decomp.)

EXAMPLE 2

2-(3-Oxo-6-pyridin-4-yl-2,3-dihydropyridazin-4-yl)-1H-benzimidazole-5-carboxylic acid

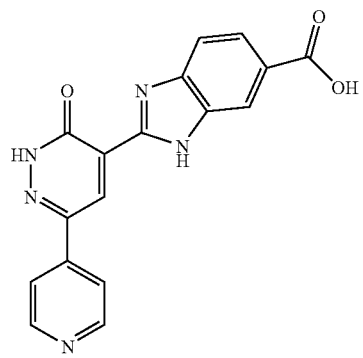

A mixture consisting of 500 mg of methyl 4-amino-3-[(3-oxo-6-pyridin-4-yl-2,3-dihydropyridazine-4-carbonyl)amino]benzoate, 6 ml of tetrahydrofuran (THF), 6 ml of methanol, 6 ml of water and 173 mg of lithium hydroxide is stirred at 50° C. for 5 hours. After cooling to room temperature, the pH is adjusted to 4-5 with 1N HCl, whereupon a precipitate separates out and is filtered off with suction and then washed with water and dried in vacuo.

Yield: 380 mg m.p.: >300° C.

EXAMPLE 3

2-(3-Oxo-6-pyridin-4-yl-2,3-dihydropyridazin-4-yl)-1H-benzimidazole-5-carboxylic acid (2-diethylaminoethyl)amide

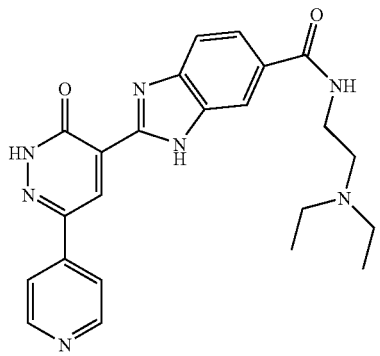

A mixture consisting of 50 mg of 2-(3-oxo-6-pyridin-4-yl-2,3-dihydropyridazin-4-yl)-3H-benzoimidazole-5-carboxylic acid, 0.065 ml of triethylamine and 1.5 ml of dimethylformamide (DMF) is stirred at room temperature for 10 minutes, mixed with 68.4 mg of O-(7-azabenzotriazol-1-yl)-N,N,N',N'-tetramethyluronium hexafluorophosphate (Hatu) and stirred at room temperature for a further 30 minutes. Then 21 mg of diethylaminoethylamine are added, and the mixture is stirred at 50° C. for 3 hours. After cooling, it is diluted with 5 ml of water, and the precipitate is filtered off with suction and stirred with isopropanol at 60° C., filtered off with suction and dried in vacuo.

Yield: 53 mg m.p.: 263° C.

EXAMPLE 4

4-(5-Chloro-1H-benzimidazol-2-yl)-6-(2-ethylaminopyrimidin-4-yl)-2H-pyridazin-3-one

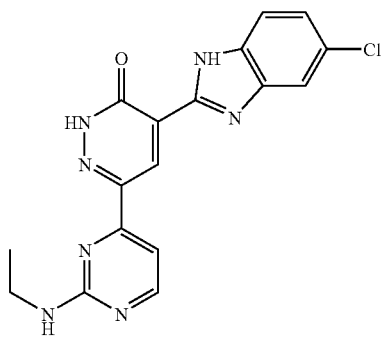

a) 1-(2-Ethylaminopyrimidin-4-yl)ethanone

A mixture of 6 g of 1-dimethylamino-4,4-dimethoxypent-1-en-3-one, 3.96 of N-ethylguanidine hydrochloride and 26 ml of 20% strength ethanolic sodium ethoxide solution is heated under reflux for 2 hours. After cooling, the solid is filtered off with suction, and the filtrate is concentrated in vacuo and mixed with 20 ml of trifluoroacetic acid and 2 ml of water and stirred at room temperature overnight. Then 50 ml of water are added, the pH is adjusted to 10 with sodium carbonate, and the mixture is extracted twice with 25 ml of ethyl acetate each time. The organic phase is dried over sodium sulfate and concentrated. The resulting oily residue is purified by column chromatography (silica gel, mobile phase: methylene chloride:methanol=98:2).

Yield: 1.9 g m.p.: 70.9° C.

b) Diethyl 2-[2-(2-ethylaminopyrimidin-4-yl)-2-oxo-ethyl]-2-hydroxy-malonate

A mixture consisting of 1.9 g of 1-(2-ethylaminopyrimidin-4-yl)ethanone and 1.86 ml of diethyl ketomalonate is heated at 110° C. for 18 hours. The mixture is purified by column chromatography (silica gel, mobile phase: methylene chloride:methanol=98:2).

Yield: 2g m.p.: resin c) Ethyl 6-(2-ethylaminopyrimidin-4-yl)-3-oxo-2,3-dihydropyridazine-4-carboxylate A mixture of 2 g of diethyl 2-[2-(2-ethylaminopyrimidin-4-yl)-2-oxo-ethyl]-2-hydroxy-malonate, 485 mg of hydrazine hydrochloride and 20 ml of ethanol is stirred under reflux for 24 hours. After cooling while stirring, the precipitate is filtered off with suction, heated in 4 ml of N-methylpyrrolidinone (NMP) at 130° C. for 3 hours and, after cooling, mixed with 15 ml of n-heptane and stirred. The precipitate is then filtered off with suction and stirred with methylene chloride, again filtered off with suction and dried.

Yield: 660 mg m.p.: 234° C.

d) 6-(2-Ethylaminopyrimidin-4-yl)-3-oxo-2,3-dihydropyridazine-4-carboxylic acid

A mixture of 400 mg of ethyl 6-(2-ethylaminopyrimidin-4-yl)-3-oxo-2,3-dihydro-pyridazine-4-carboxylate, 2 ml of THF, 2 ml of water, 2 ml of methanol and 100 mg of lithium hydroxide is stirred at room temperature for 1 hour, and the volatile constituents are removed in vacuo. A pH of 4 is adjusted by dropwise addition of 2N hydrochloric acid, and the precipitate which has formed is filtered off with suction, stirred with 10 ml of isopropanol and filtered off with suction and dried.

Yield: 200 mg m.p.: 322° C.

e) 6-(2-Ethylaminopyrimidin-4-yl)-3-oxo-2,3-dihydropyridazine-4-carboxylic acid (2-amino-4-chlorophenyl)amide A solution of 110 mg of 6-(2-ethylaminopyrimidin-4-yl)-3-oxo-2,3-dihydropyridazine-4-carboxylic acid, 2 ml of DMF and 0.17 ml of triethylamine is mixed with 192 mg of Hatu and stirred at room temperature for 30 minutes. Then 66 mg of 4-chloro-phenylenediamine are added, and the mixture is stirred at room temperature overnight. 5 ml of water are added to the mixture, and the precipitate is briefly stirred and then filtered off with suction and dried.

Yield: 57 mg m.p.: >300° C. (decomp.)

f) 4-(5-Chloro-1H-benzoimidazol-2-yl)-6-(2-ethy-laminopyrimidin-4-yl)-2H -pyridazin-3-one 6-(2-Ethylaminopyrimidin-4-yl)-3-oxo-2,3-dihydropyridazine-4-carboxylic acid (2amino-4-chlorophenyl)amide (50 mg) are stirred in 1 ml of glacial acetic acid at 100° C. for 3 hours. After cooling, the precipitate is filtered off with suction, stirred with aqueous sodium bicarbonate solution and again filtered off with suction, washed with water and dried in vacuo.

Yield: 15 mg m.p. >300° C. (decomp.)

The following examples 5-14, 17-23, 26-33, 38 and 40 are prepared in analogy to example 1:

EXAMPLE 5

4-(6-Chloro-1H-benzimidazol-2-yl)-6-pyridin-4-yl-2H-pyridazin-3-one

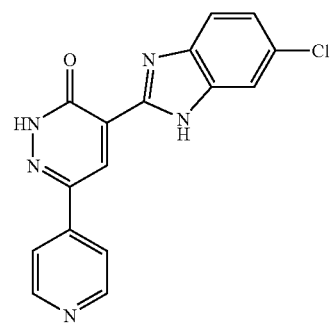

m.p. >300° C. (decomp.)

EXAMPLE 6

4-(6-Trifluoromethyl-1H-benzimidazol-2-yl)-6-pyridin-4-yl-2H-pyridazin-3-one

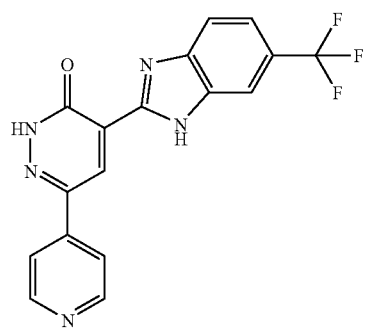

m.p. >300° C. (decomp.)

EXAMPLE 7

4-(6-Methoxy-1H-benzimidazol-2-yl)-6-pyridin-yl-2H-pyridazin-3-one

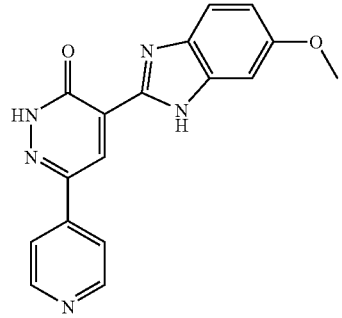

m.p. >300° C. (decomp.)

EXAMPLE 8

2-(3-Oxo-6-pyridin-4-yl-2,3-dihydropyridazin-4-yl)-1H-benzimidazole-5-carboxylic acid (2-cyclohexy-laminoethyl)amide

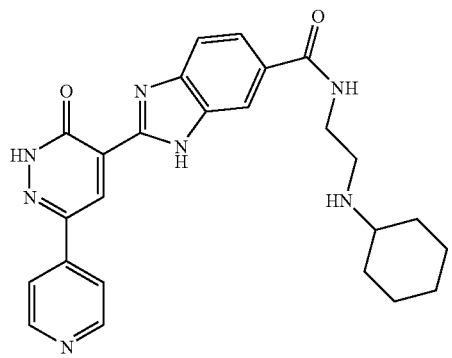

m.p. 271° C.

EXAMPLE 9

2-(3-Oxo-6-pyridin-4-yl-2,3-dihydropyridazin-4-yl)-1H-benzimidazole-5-carboxylic acid [3-(4-methylpiperazin-1-yl)propyl]amide

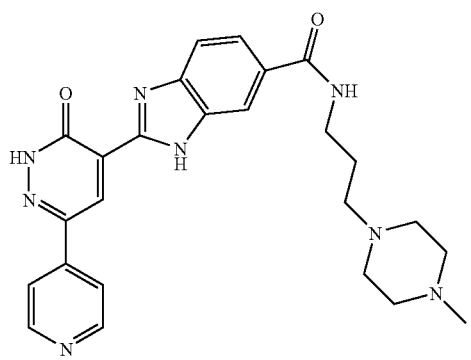

m.p. >30° C. (decomp.)

EXAMPLE 10

2-(3-Oxo-6-pyridin-4-yl-2,3-dihydropyridazin-4-yl)-1H-benzimidazole-5-carboxylic acid (3-hydroxypropyl)amide

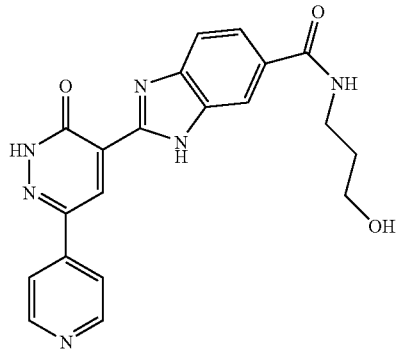

m.p. >300° C. (decomp.)

EXAMPLE 11

4-(5-Chloro-1H-benzimidazol-2-yl)-6-methyl-2H-pyridazin-3-one

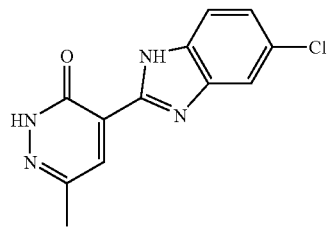

m.p. >300° C. (decomp.)

EXAMPLE 12

2-(3-Oxo-6-pyridin-4-yl-2,3-dihydropyridazin-4-yl)-1H-benzimidazole-5-carboxylic acid (3-cyclohexylaminopropyl)amide

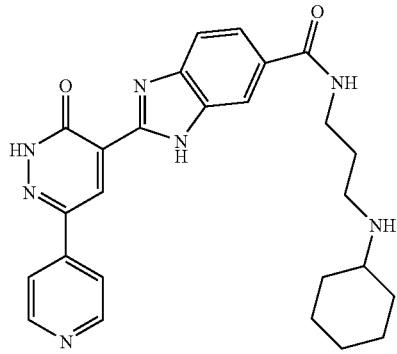

m.p.: resin

EXAMPLE 13

2-(3-Oxo-6-pyridin-4-yl-2,3-dihydropyridazin-4-yl)-1H-benzimidazole-5-carboxylic acid (3-imidazol-1-yl-propyl)amide

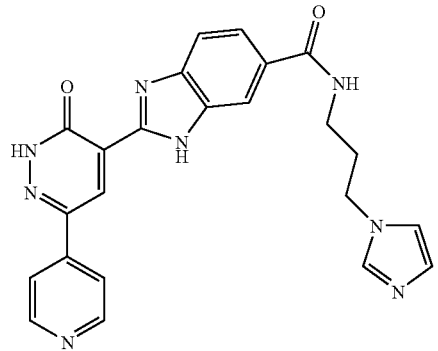

m.p.: resin

EXAMPLE 14

4-(5-Chloro-1H-benzimidazol-2-yl)-6-(2-methylaminopyrimidin-4-yl)-2H-pyridazin-3-one

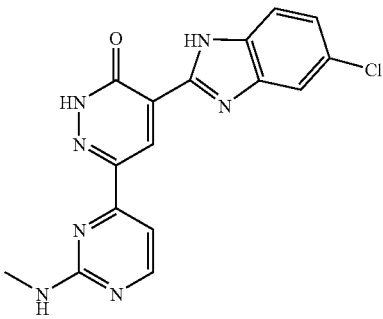

m.p.: >300° C. (decomp.)

EXAMPLE 15

4-(6-Chloro-1H-benzimidazol-2-yl)-6-(4-hydroxy-3,5-dimethylphenyl)-2H-pyridazin-3-one

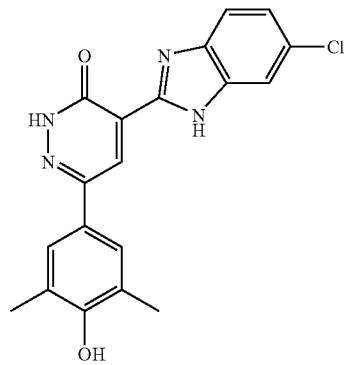

a) Mixture of 6-chloro-3-oxo-2,3-dihydropyridazine-4-carboxylic acid (2-amino-5-chlorophenyl)amide and 6-chloro-3-oxo-2,3-dihydropyridazine-4-carboxylic acid (2-amino-4-chlorophenyl)amide 6-Chloro-3-oxo-2,3-dihydropyridazine-4-carboxylic acid (5 g; 28.6 mmol) is dissolved in a mixture of tetrahydrofuran (250 ml) and DMF (1 ml) and cooled to 8° C. in an ice bath, and oxalyl chloride (19.42 g; 153 mmol) is added dropwise. The mixture is stirred at RT for 2 h, and the solvent is stripped off in vacuo. The residue is dissolved in THF, and the volatile constituents are again stripped off in vacuo at RT. The residue is dissolved in tetrahydrofuran/DMF, and 4-chloro-phenylenediamine (4.08 g; 28.6 mmol) and potassium carbonate (7.92 g; 57.3 mmol) are added. After stirring at RT for 16 hours, the volatile constituents are removed in vacuo, the residue is taken up in water, and the solution is adjusted to pH 2 with 2N hydrochloric acid. The precipitate is filtered off with suction, and the product is purified by column chromatography (silica gel, ethyl acetate/n-heptane, gradient 0-80%).

Yield: 1.0 g.

b) 6-Chloro-4-(6-chloro-1H-benzimidazol-2-yl)-2H-pyridazin-3-one

A mixture of 6-chloro-3-oxo-2,3-dihydropyridazine-4-carboxylic acid (2-amino-5-chlorophenyl)amide and 6-chloro-3-oxo-2,3-dihydropyridazine-4-carboxylic acid (2-amino-4-chlorophenyl)amide (1.0 g; 1.67 mmol) is dissolved in 100 ml of glacial acetic acid and heated at 120° C. for 90 min. A precipitate separates out on cooling and is filtered off with suction and dried in vacuo at 40° C.

Yield: 315 mg.

c) 6-Chloro-4-[6-chloro-1-(2-trimethylsilanylethoxymethyl)-1H-benzimidazol-2-yl]-2-(2-trimethylsilanylethoxymethyl)-2H-pyridazin-3-one 6-Chloro-4-(6-chloro-1H-benzimidazol-2-yl)-2H-pyridazin-3-one (315 mg; 1.12 mmol) is dissolved in DMF (8.3 ml), cesium carbonate (1.1 g; 3.36 mmol) and (2-chloromethoxyethyl)trimethylsilane (467 mg; 2.8 mmol) are added, and the mixture is stirred at 60° C. for 2 h, cooled and filtered, and the product is purified by column chromatography (RP-HPLC, gradient of 0-100% acetonitrile in water (+0.01% trifluoroacetic acid)).

Yield: 513 mg.

d) 4-[6-Chloro-1-(2-trimethylsilanylethoxymethyl)-1H-benzimidazol-2-yl]-6-(4-hydroxy-3,5-dimethylphenyl)-2-(2-trimethylsilanylethoxymethyl)-2H-pyridazin -3-one 6-Chloro-4-[6-chloro-1-(2-trimethylsilanylethoxymethyl)-1H-benzimidazol-2-yl]-2-(2-trimethylsilanylethoxymethyl)-2H-pyridazin-3-one (100 mg; 0.185 mmol) and tetrakis(triphenylphosphine) palladium(0) (0.15 equivalents) are dissolved in DME, and argon is passed in for 10 min. 2,6-Dimethyl-4-(4,4,5,5-tetramethyl-1,3,2-dioxaborolan-2-yl)phenol (1 equivalent) and 2M aqueous sodium carbonate solution (2 equivalents) are added and the mixture is heated at 95° C. for 5 hours. The volatile constituents are removed in vacuo, the residue is taken up in DMF, and the product the product is purified by column chromatography (RP-HPLC, gradient of 0-100% acetonitrile in water (+0.01% trifluoroacetic acid)).

Yield: 64 mg e) 4-(6-Chloro-1H-benzimidazol-2-yl)-6-(4-hydroxy-3,5-dimethylphenyl)-2H-pyridazin-3-one 4-[6-Chloro-1-(2-trimethylsilanylethoxymethyl)-1H-benzimidazol-2-yl]-6-(4-hydroxy-3,5-dimethylphenyl)-2-(2-trimethylsilanylethoxymethyl)-2H-pyridazin-3-one is stirred in dichloromethane:trifluoroacetic acid/1:1 at RT for 30 min. The solvent is stripped off in vacuo, and the residue is dissolved in methanol, and 2M sodium hydroxide solution is added. The solution is stirred at RT for 30 min. After the reaction is complete, water is added and 2N hydrochloric acid is used for acidification. The precipitated product is filtered off with suction and purified by column chromatography (RP-HPLC, gradient of 0-100% acetonitrile in water (+0.01% trifluoroacetic acid)).

Yield: 12.5 mg. MS (ES+) m/z 367 (M+H).

The following examples 16, 24, 25, 34-37, 39 and 41 are prepared as in example 15

EXAMPLE 16

4-(6-Chloro-1H-benzimidazol-2-yl)-6-(4-hydroxy-3-methoxyphenyl)-2H-pyridazin-3-one

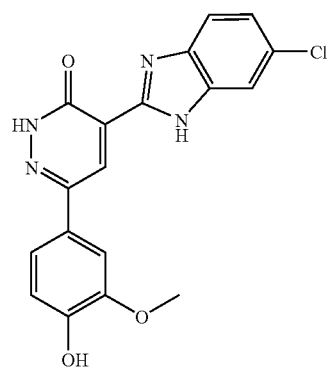

MS (ES+) m/z 369 (M+H).

EXAMPLE 17

4-(7-Methyl-1H-benzimidazol-2-yl)-6-pyridin-4-yl-2H-pyridazin-3-one

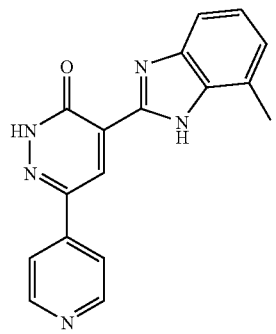

m.p.: >350° C. (decomp.)

EXAMPLE 18

4-(5,6-Dimethyl-1H-benzimidazol-2-yl)-6-pyridin-4-yl-2H-pyridazin-3-one

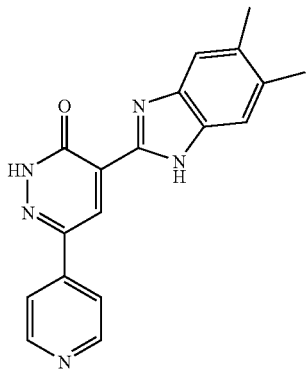

m.p.: >350° C. (decomp.)

EXAMPLE 19

4-[5-(4-Methylpiperazin-1-yl)-1H-benzimidazol-2-yl]-6-pyridin-4-yl-2H-pyridazin-3-one

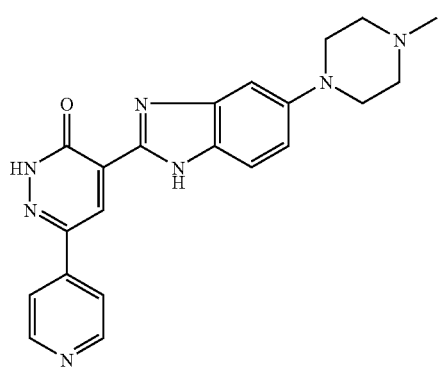

m.p.: >350° C. (decomp.)

EXAMPLE 20

4-(5-Fluoro-1H-benzimidazol-2-yl)-6-pyridin-4-yl-2H-pyridazin-3-one

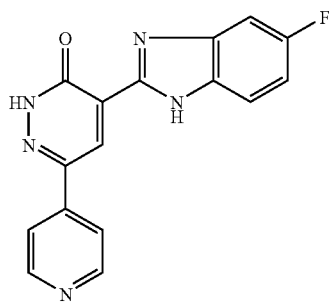

m.p.: >350° C. (decomp.)

EXAMPLE 21

4-(5-Cyano-1H-benzimidazol-2-yl)-6-pyridin-4-yl-2H-pyridazin-3-one

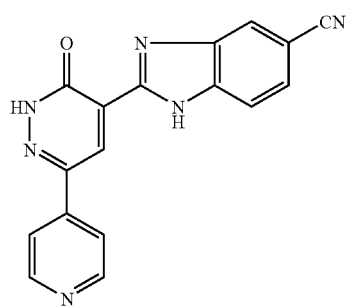

m.p.: >350° C. (decomp.)

EXAMPLE 22

4-(5-Bromo-1H-benzimidazol-2-yl)-6-pyridin-4-yl-2H-pyridazin-3-one

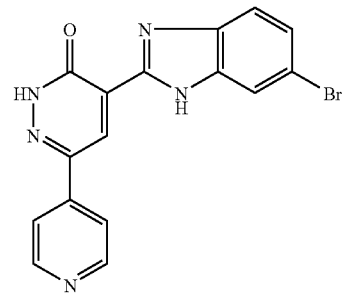

m.p.: >350° C. (decomp.)

EXAMPLE 23

6-Chloro-4-(3H-imidazo[4,5-c]pyridin-2-yl)-2H-pyridazin-3-one

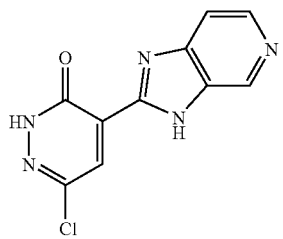

MS (ES+) m/z 248 (M+H).

EXAMPLE 24

6-(4-Hydroxy-3-methoxyphenyl)-4-(6-trifluoromethyl-1H-benzimidazol-2-yl)-2H-pyridazin-3-one

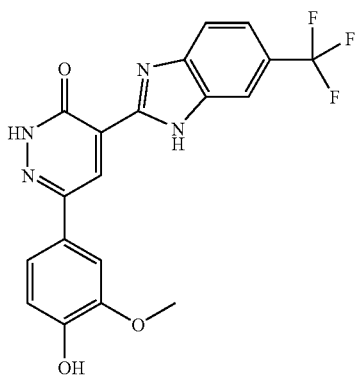

MS (ES+) m/z 403 (M+H).

EXAMPLE 25

6-(4-Hydroxy-3,5-dimethylphenyl)-4-(6-trifluoromethyl-1H-benzimidazol-2-yl)-2H-pyridazin-3-one

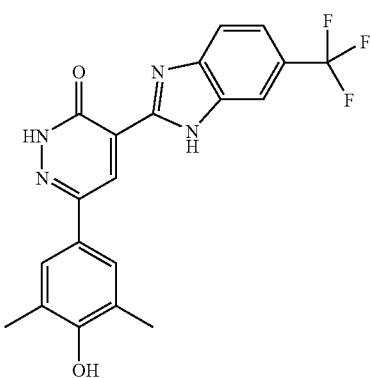

MS (ES+) m/z 401 (M+H).

EXAMPLE 26

6-(2-Butylaminopyrimidin-4-yl)-4-(6-chloro-1H-benzimidazol-2-yl)-2H-pyridazin-3-one

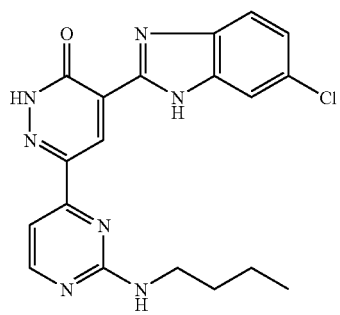

m.p.: 305° C.

EXAMPLE 27

6-(2-Butylaminopyrimidin-4-yl)-4-(6-trifluoromethyl-1H-benzimidazol-2-yl)-2H-pyridazin-3-one

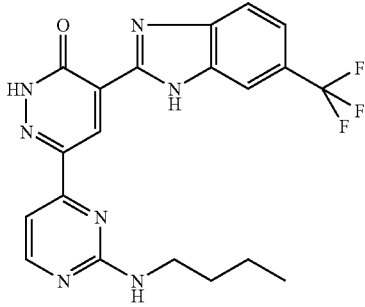

m.p.: 288° C.

EXAMPLE 28

4-(1H-Benzimidazol-2-yl)-6-pyridin-4-yl-2H-pyridazin-3-one

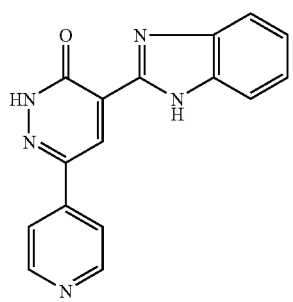

m.p.: >350° C. (decomp.)

EXAMPLE 29

4-(6-Chloro-1H-benzimidazol-2-yl)-6-[2-((R)-1-phenylethylamino)pyrimidin-4-yl]-2H-pyridazin-3-one

CHIRAL

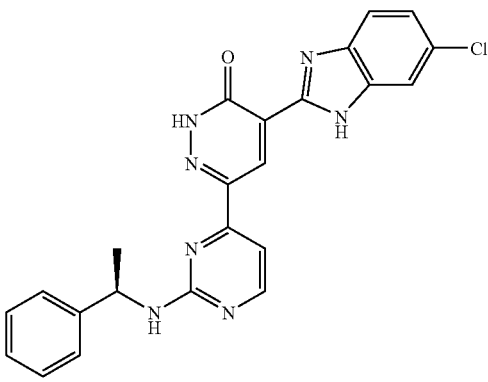

MS (ES+) m/z 444 (M+H)

EXAMPLE 30

4-(5,6-Dichloro-1H-benzimidazol-2-yl)-6-pyridin-4-yl-2H-pyridazin-3-one; compound with acetic acid

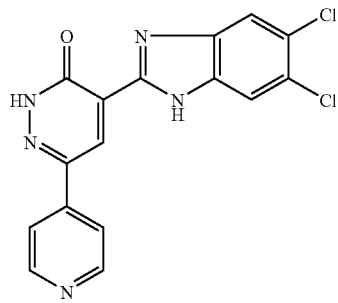

MS (ES+) m/z 358 (M+H)

EXAMPLE 31

4-(6-Chloro-5-fluoro-1H-benzimidazol-2-yl)-6-pyridin-4-yl-2H-pyridazin-3-one; compound with acetic acid

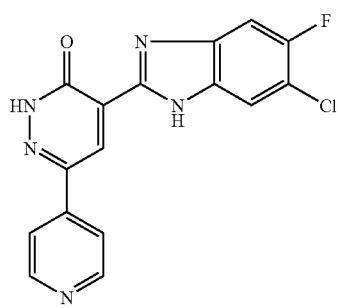

MS (ES+) m/z 342 (M+H)

EXAMPLE 32

4-(6-Chloro-5-methyl-1H-benzimidazol-2-yl)-6-pyridin-4-yl-2H-pyridazin-3-one; compound with acetic acid

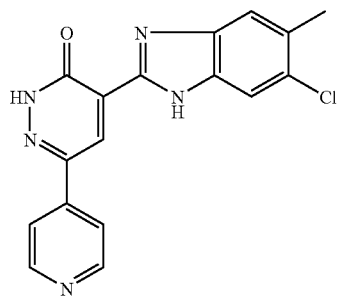

MS (ES+) m/z 338 (M+H)

EXAMPLE 33

4-(5,7-Difluoro-1H-benzimidazol-2-yl)-6-pyridin-4-yl-2H-pyridazin-3-one; compound with acetic acid

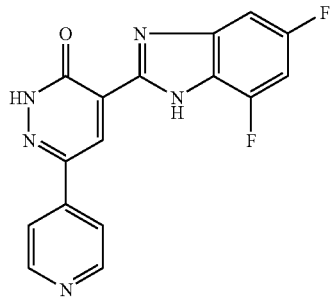

MS (ES+) m/z 326 (M+H)

EXAMPLE 34

4-(5-Chloro-6-methyl-1H-benzimidazol-2-yl)-6-(4-hydroxy-3-methoxyphenyl)-2H-pyridazin-3-one

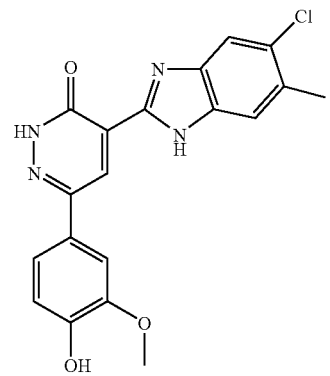

MS (ES+) m/z 383 (M+H)

EXAMPLE 35

6-[2-(2-Morpholin-4-yl-ethylamino)pyrimidin-4-yl]-4-(6-trifluoromethyl-1H-benzimidazol-2-yl)-2H-pyridazin-3-one; compound with trifluoroacetic acid

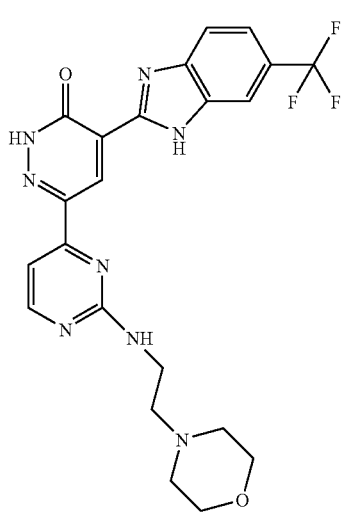

MS (ES+) m/z 487 (M+H)

EXAMPLE 36

4-(5,6-Dichloro-1H-benzimidazol-2-yl-6-(4-hydroxy-3-methoxyphenyl)-2H-pyridazin-3-one

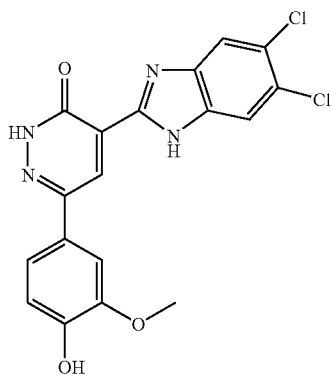

MS (ES+) m/z 403 (M+H)

EXAMPLE 37

2-[6-(4-Hydroxy-3-methoxyphenyl)-3-oxo-2,3-dihydropyridazin-4-yl]-3H-benzimidazole-5-carboxylic acid

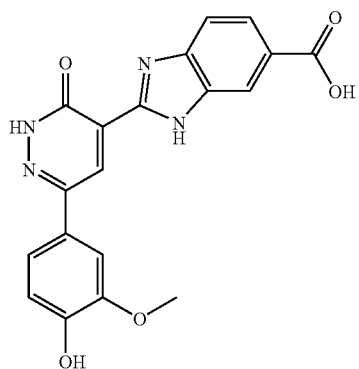

MS (ES+) m/z 379 (M+H)

EXAMPLE 38

4-(3H-Imidazol[4,5-c]pyridin-2-yl)-6-pyridin-4-yl-2H-pyridazin-3-one

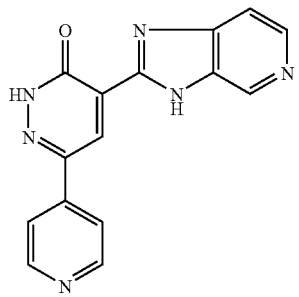

MS (ES+) m/z 291 (M+H)

EXAMPLE 39

6-[6-Methyl-2-(2-morpholin-4-yl-ethylamino)pyrimidin-4-yl]-4-(6-trifluoromethyl-1H-benzimidazol-2-yl)-2H-pyridazin-3-one

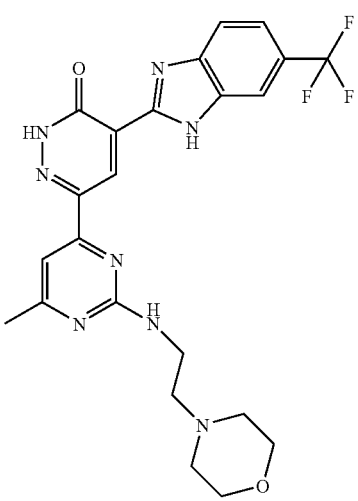

MS (ES+) m/z 501 (M+H)

EXAMPLE 40

4-(6-Chloro-1H-benzimidazol-2-yl)-6-(2-methylsulfanylpyrimidin-4-yl)-2H-pyridazin-3-one

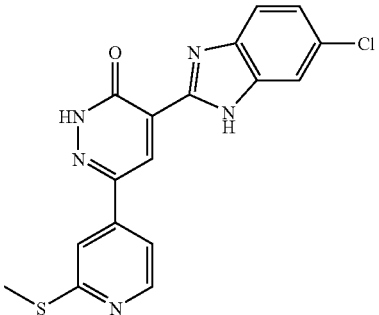

MS (ES+) m/z 371 (M+H)

EXAMPLE 41

6-(4-Hydroxy-3,5-dimethylphenyl)-4-(7-methyl-1H-benzimidazol-2-yl)-2H-pyridazin-3-one

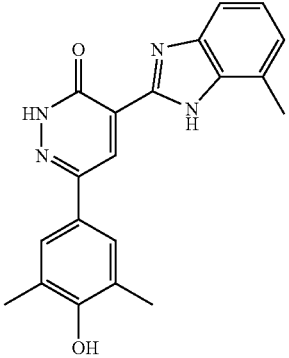

MS (ES+) m/z 347 (M+H)

Functional Measurements to Ascertain $IC_{50}$ Values:

A 96-well streptavidin-coated flashplate is used to assay potency of compounds according to formula (I) against CDK2/Cyclin E kinase. To carry out the assay, biotinylated-Rb peptide substrate Biotin-SACPLNLPLQNNHTAAD-MYLSPVRSPKKKGSTTR-OH) is solubilized at 1 mM in kinase buffer (Hepes 50 mM, NaCl 1 mM, MgCl2 5 mM pH 7.5) as a stock solution conserved at −20° C. in aliquots of 110 µl. The day of the experiment, an aliquot of this solution is thawed and diluted to 14.3 µM in kinase buffer, containing 1 mM dithithreitol (DTT) added in the buffer extemporarily.

70 µl of this solution is added in each well of the flashplate in order to achieve a final concentration of 10 µM (100 µl reactionnal volume). Serial dilutions of inhibitors are prepared in DMSO from 10 mM stock solutions in order to achieve 1000 µM, 333.3 µM, 111.1 µM, 37.03 µM, 12.35 µM, 4.11 µM and 1.37 µM and all rediluted in kinase buffer+DTT in order to achieve 100 µM, 33.3 µM, 11.1 µM, 3.7 µM, 1.24 µM, 0.41 µM and 0.14 µM in DMSO 10% buffer (vol/vol). 10 µl of each of these solutions (or 10 µl of buffer+DTT for controls) are transferred to the testplate wells in order to achieve 10 µM, 3.33 µM, 1.11 µM, 0.37 µM, 0.12 µM, 0.04 µM and 0.01 µM as final concentrations, 1% DMSO (vol/vol). In each well, 10 µl of a solution of a mix of $^{33}P\gamma ATP/ATP$ are added in order to achieve 1 µM final concentration and a total of 1 µCi. The kinase reaction is initiated by addition of 10 µl of a solution at 200 nM of CDK2/Cyclin E in kinase buffer+DTT (or buffer+DTT for blanks) in order to achieve 20 nM final concentration. After addition of each reagent, the testplate is shaked. The plates are incubated 30 minute at 30° C. with a shaking at 650 rpm. At the end of the incubation, the plates are washed 3 times with 300 µl of PBS (without calcium and magnesium) per well. The incorporation of $^{33}P$ to the peptide is measured by scintillation counting.

The results from the CDK2/Cyclin-E assay can be found in the following table:

| Example | IC50 [µM] |
|---------|-----------|
| 1 | 0.124 |
| 5 | 0.026 |
| 6 | 0.214 |

What is claimed is:

1. A compound of the formula (I)

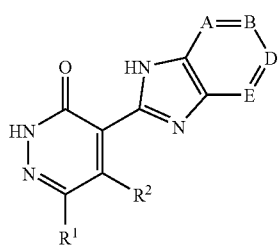

(I)

wherein:
A is $CR^3$ or N;
B is $CR^4$ or N;
D is $CR^5$ or N;
E is $CR^6$ or N;
where one of A, B, D, and E is N;
$R^1$ is halogen;
unsubstituted or at least monosubstituted $C_1$-$C_{10}$-alkyl,
where the substituents are selected from the group consisting of: halogen, —CN, $NO_2$, —$OR^7$, —$C(O)R^7$, —$C(O)OR^7$, —O—$C(O)R^7$, —$NR^7R^8$, —NHC(O)$R^7$, —$C(O)NR^7R^8$, —NHC(S)$R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, heterocyclyl, trifluoromethyl and trifluoromethoxy,
and heterocyclyl, aryl and heteroaryl may in turn be at least monosubstituted by $C_1$-$C_6$-alkyl, $C_1$-$C_6$-alkoxy, halogen, trifluoromethyl, trifluoromethoxy or OH;
unsubstituted or at least monosubstituted aryl or heteroaryl,
where the substituents are selected from the group consisting of: halogen, —CN, $NO_2$, —$CH_2$—$R^7$, —$OR^7$, —$C(O)R^7$, —$C(O)OR^7$, —O—$C(O)R^7$, —$NR^7R^8$, —NHC(O)$R^7$, —$C(O)NR^7R^8$, —NHC(S)$R^7$, —$C(S)NR^7R^8$, —$SR^7$, —$S(O)R^7$, —$SO_2R^7$, —$NHSO_2R^7$, —$SO_2NR^7R^8$, —O—$SO_2R^7$, —$SO_2$—O—$R^7$, aryl, heteroaryl, trifluoromethyl and trifluoromethoxy,
and aryl and heteroaryl may in turn be at least monosubstituted by $C_1$-$C_6$-alkyl, $C_1$-$C_6$-alkoxy, halogen, trifluoromethyl, trifluoromethoxy or OH;
$R^2$ is hydrogen or $C_1$-$C_{10}$-alkyl;
$R^3$, $R^4$, $R^5$ and $R^6$ are independently of one another selected from the group consisting of hydrogen, halogen, —CN, $NO_2$, —$CH_2$—$R^8$, —$OR^8$, —$C(O)R^8$, —$C(O)OR^8$, —O—$C(O)R^8$, —$NR^7R^8$; —NHC(O)$R^8$, —$C(O)NR^7R^8$, —NHC(S)$R^8$, —$C(S)NR^7R^8$, —$SR^8$, —$S(O)R^8$, —$SO_2R^8$, —$NHSO_2R^8$, —$SO_2NR^7R^8$, —O—$SO_2R^8$, —$SO_2$—O—$R^8$, aryl, heteroaryl, heterocyclyl, trifluoromethyl and trifluoromethoxy,
and heterocyclyl, aryl and heteroaryl may in turn be at least monosubstituted by $C_1$-$C_6$-alkyl, $C_1$-$C_6$-alkoxy, oxo, halogen, trifluoromethyl, trifluoromethoxy or OH;
$R^7$ and $R^8$ are independently of one another:
H;
unsubstituted or at least monosubstituted $C_1$-$C_{10}$-alkyl, $C_2$-$C_{10}$-alkenyl, $C_2$-$C_{10}$-alkynyl, heterocyclyl, aryl or heteroaryl,
where the substituents are selected from the group consisting of: heteroaryl, heterocyclyl, aryl, halogen, OH, oxo, $C_1$-$C_{10}$-alkoxy, ($C_1$-$C_{10}$-alkyl)thio-, COOH, —COO—($C_1$-$C_6$-alkyl), —$CONH_2$, trifluoromethyl, trifluoromethoxy; CN, $NH_2$, ($C_1$-$C_{10}$-alkyl)amino- and di-($C_1$-$C_{10}$-alkyl)amino-,
and heterocyclyl, aryl and heteroaryl may in turn be at least monosubstituted by $C_1$-$C_6$-alkyl, $C_1$-$C_6$-alkoxy, oxo, trifluoromethyl, trifluoromethoxy, fluorine, chlorine or OH;
heteroaryl is a 5 to 10-membered, aromatic, mono- or bicyclic heterocycle which comprises one or more heteroatoms selected from N, O and S;
aryl is a 5 to 10-membered, aromatic, mono- or bicyclic system;
heterocyclyl is a 5 to 10-membered, nonaromatic, mono- or bicyclic heterocycle which comprises one or more heteroatoms selected from N, O and S;
or a physiologically tolerated salt thereof.

2. A compound according to claim 1, wherein:
A is $CR^3$;
B is $CR^4$ or N;
D is $CR^5$ or N;
E is $CR^6$;
where one of B and D is N;

$R^1$ is fluorine; chlorine; bromine;
unsubstituted or at least monosubstituted $C_1$-$C_6$-alkyl,
where the substituents are selected from the group consisting of: halogen, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, heterocyclyl, trifluoromethyl and trifluoromethoxy,
and heterocyclyl, aryl and heteroaryl may in turn be at least monosubstituted by $C_1$-$C_6$-alkyl, $C_1$-$C_6$-alkoxy, halogen, trifluoromethyl, trifluoromethoxy or OH;
unsubstituted or at least monosubstituted aryl or heteroaryl,
where the substituents are selected from the group consisting of: halogen, —$CH_2$—$R^7$, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, trifluoromethyl and trifluoromethoxy,
and aryl and heteroaryl may in turn be at least monosubstituted by $C_1$-$C_6$-alkyl, $C_1$-$C_6$-alkoxy, halogen, trifluoromethyl, trifluoromethoxy or OH;
$R^2$ is hydrogen or $C_1$-$C_6$-alkyl;
$R^3$, $R^4$, $R^5$ and $R^6$ are independently of one another selected from the group consisting of:
hydrogen, halogen, —CN, —$CH_2$—$R^8$, —$OR^8$, —$C(O)R^8$, —$C(O)OR^8$, —$NR^8H$, —$NR^8(C_1$-$C_6$-alkyl-), —$C(O)NR^8H$, —$SR^8$, —$SO_2NR^8H$, —$SO_2$—$R^8$, aryl, heteroaryl, heterocyclyl, trifluoromethyl and trifluoromethoxy,
and heterocyclyl, aryl and heteroaryl may in turn be at least monosubstituted by $C_1$-$C_6$-alkyl, $C_1$-$C_6$-alkoxy, oxo, halogen, trifluoromethyl, trifluoromethoxy or OH;
$R^7$ and $R^8$ are independently of one another:
H;
unsubstituted or at least monosubstituted $C_1$-$C_6$-alkyl, heterocyclyl, phenyl or heteroaryl,
where the substituents are selected from the group consisting of: heteroaryl, heterocyclyl, phenyl, fluorine, chlorine, bromine, OH, $C_1$-$C_6$-alkoxy, trifluoromethyl, trifluoromethoxy, $NH_2$, ($C_1$-$C_6$-alkyl)amino- and di-($C_1$-$C_6$-alkyl)amino-,
and heterocyclyl, phenyl and heteroaryl may in turn be at least monosubstituted by $C_1$-$C_3$-alkyl, $C_1$-$C_3$-alkoxy, oxo, trifluoromethyl, trifluoromethoxy, fluorine, chlorine or OH;
heteroaryl is imidazolyl, thiophenyl, furanyl, oxazolyl, isoxazolyl, pyridinyl, pyrimidinyl, pyrazolyl, benzo[b]thiophenyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzodioxolyl;
aryl is naphthyl, indanyl or phenyl;
heterocyclyl is 2-oxoazepanyl, tetrahydrofuranyl, 1,3-dioxolanyl, morpholinyl, pyrrolidinyl, piperazinyl or piperidinyl;
or a physiologically tolerated salt thereof.

3. A compound according to claim 1, wherein:
A is $CR^3$;
B is N;
D is $CR^5$;
E is $CR^6$;
$R^1$ is chlorine;
unsubstituted or at least monosubstituted $C_1$-$C_6$-alkyl,
where the substituents are selected from the group consisting of: fluorine, chlorine, OH, $C_1$-$C_6$-alkoxy, $NH_2$, ($C_1$-$C_6$-alkyl)amino-, di-($C_1$-$C_6$-alkyl)amino-, —NH (heterocyclyl-($C_1$-$C_6$-alkyl-)), —NH(aryl-($C_1$-$C_6$-alkyl-)), heterocyclyl, aryl and heteroaryl,
and heterocyclyl, aryl and heteroaryl may in turn be at least monosubstituted by $C_1$-$C_4$-alkyl, $C_1$-$C_4$-alkoxy, fluorine, chlorine, trifluoromethyl, trifluoromethoxy or OH;
unsubstituted or at least monosubstituted phenyl, pyridinyl, pyrimidinyl, pyrazolyl, thiophenyl, oxazolyl, isoxazolyl, benzo[b]thiophenyl, 1,3-benzodioxolyl or thiazolo[3,2-b][1,2,4]-triazolyl,
where the substituents are selected from the group consisting of: halogen, —$CH_2$—$R^7$, —$OR^7$, —$C(O)R^7$, —$C(O)OR^7$, —$NR^7H$, —$NR^7(C_1$-$C_6$-alkyl-), —$C(O)NR^7H$, —$SR^7$, aryl, heteroaryl, trifluoromethyl and trifluoromethoxy,
and aryl and heteroaryl may in turn be at least monosubstituted by $C_1$-$C_6$-alkyl, $C_1$-$C_6$-alkoxy, halogen, trifluoromethyl, trifluoromethoxy or OH;
$R^2$ is hydrogen;
$R^3$, $R^4$, $R^5$ and $R^6$ are independently of one another selected from the group consisting of:
hydrogen, fluorine, chlorine, bromine, —CN, —$CH_2$—$R^8$, —$OR^8$, —$C(O)R^8$, —$C(O)OR^8$, —$NR^8H$, —$NR^8(C_1$-$C_6$-alkyl-), —$C(O)NR^8H$, —$SR^8$, —$SO_2NR^8H$, $SO_2$—$R^8$, heterocyclyl, trifluoromethyl and trifluoromethoxy,
and heterocyclyl may in turn be at least monosubstituted by $C_1$-$C_6$-alkyl, $C_1$-$C_6$-alkoxy, halogen, trifluoromethyl, trifluoromethoxy or OH;
$R^7$ and $R^8$ are independently of one another:
H;
unsubstituted or at least monosubstituted $C_1$-$C_6$-alkyl, heterocyclyl, phenyl or heteroaryl,
where the substituents are selected from the group consisting of: heteroaryl, heterocyclyl, phenyl, fluorine, chlorine, bromine, OH, $C_1$-$C_6$-alkoxy, trifluoromethyl, trifluoromethoxy, $NH_2$, ($C_1$-$C_6$-alkyl)amino- and di-($C_1$-$C_6$-alkyl)amino-
and heterocyclyl, phenyl and heteroaryl may in turn be at least monosubstituted by $C_1$-$C_3$-alkyl, $C_1$-$C_3$-alkoxy, oxo, trifluoromethyl, trifluoromethoxy, fluorine, chlorine or OH;
heteroaryl is imidazolyl, thiophenyl, furanyl, oxazolyl, isoxazolyl, pyridinyl, pyrimidinyl, pyrazolyl, benzo[b]thiophenyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzodioxolyl;
aryl is naphthyl, indanyl or phenyl;
heterocyclyl is 2-oxoazepanyl, tetrahydrofuranyl, 1,3-dioxolanyl, morpholinyl, pyrrolidinyl, piperazinyl or piperidinyl;
or a physiologically tolerated salt thereof.

4. A compound according to claim 1, wherein:
A is $CR^3$;
B is N;
D is $CR^5$;
E is $CR^6$;
$R^1$ is unsubstituted or at least monosubstituted phenyl, pyridinyl, pyrimidinyl, pyrazolyl, thiophenyl, oxazolyl, isoxazolyl, benzo[b]thiophenyl, benzodioxolyl or thiazolo[3,2-b][1,2,4]-triazolyl,
where the substituents are selected from the group consisting of: halogen, $C_1$-$C_6$-alkyl, phenyl-($C_1$-$C_6$-alkyl)-, —OH, $C_1$-$C_6$-alkoxy, ($C_1$-$C_6$-alkyl)thio-, —O-phenyl, —C(O)OH, —C(O)O—($C_1$-$C_6$-alkyl), —$NH_2$, —N($C_1$-$C_6$-alkyl)$_2$, —NH($C_1$-$C_6$-alkyl), —NH(amino-($C_1$-$C_6$-alkyl-)), —NH(($C_1$-$C_6$-alkyl) amino-($C_1$-$C_6$-alkyl-)), —NH(di-($C_1$-$C_6$-alkyl) amino-($C_1$-$C_6$-alkyl-)), —NH(heterocyclyl-($C_1$-$C_6$- alkyl-)), —NH(heteroaryl-($C_1$-$C_6$-alkyl-)), —NH(phenyl-($C_1$-$C_6$-alkyl-)), —C(O)$NH_2$, —C(O)NH—($C_1$-$C_6$-alkyl), trifluoromethyl, trifluoromethoxy, phenyl and heteroaryl, and heterocyclyl, phenyl and heteroaryl may in turn be at least monosubstituted by $C_1$-$C_3$-alkyl, $C_1$-$C_3$-alkoxy, fluorine, chlorine, trifluoromethyl, trifluoromethoxy or OH;

$R^2$ is hydrogen;

$R^3$, $R^4$, $R^5$ and $R^6$ are independently of one another selected from the group consisting of:

hydrogen, fluorine, chlorine, bromine, —CN, $C_1$-$C_6$-alkyl, —OH, $C_1$-$C_6$-alkoxy, —C(O)OH, —C(O)O—($C_1$-$C_6$-alkyl), —$NH_2$, —N($C_1$-$C_6$-alkyl)$_2$, —NH($C_1$-$C_6$-alkyl), —NH(amino-($C_1$-$C_6$-alkyl-)), —NH(hydroxy-($C_1$-$C_6$-alkyl-)), —NH(($C_1$-$C_6$-alkyl)amino-($C_1$-$C_6$-alkyl-)), —NH(di-($C_1$-$C_6$-alkyl)amino-($C_1$-$C_6$-alkyl-)), —NH(heterocyclyl-($C_1$-$C_6$-alkyl-)), —NH(heteroaryl-($C_1$-$C_6$-alkyl-)), —NH(phenyl-($C_1$-$C_6$-alkyl-)), —C(O)$NH_2$, —C(O)NH—($C_1$-$C_6$-alkyl), —C(O)N($C_1$-$C_6$-alkyl)$_2$, —C(O)NH($C_1$-$C_6$-alkyl), —C(O)NH(amino-($C_1$-$C_6$-alkyl-)), —C(O)NH(hydroxy-($C_1$-$C_6$-alkyl-)), —C(O)NH(($C_1$-$C_6$-alkyl)amino-($C_1$-$C_6$-alkyl-)), —C(O)NH(di-($C_1$-$C_6$-alkyl)amino-($C_1$-$C_6$-alkyl-)), —C(O)NH(heterocyclyl-($C_1$-$C_6$-alkyl-)), —C(O)NH(heteroaryl-($C_1$-$C_6$-alkyl-)), —C(O)NH(phenyl-($C_1$-$C_6$-alkyl-)), heterocyclyl, trifluoromethyl and trifluoromethoxy, and heteroaryl, heterocyclyl and phenyl may in turn be at least monosubstituted by $C_1$-$C_6$-alkyl, $C_1$-$C_6$-alkoxy, halogen, trifluoromethyl, trifluoromethoxy or OH;

heteroaryl is imidazolyl, thiophenyl, furanyl, oxazolyl, isoxazolyl, pyridinyl, pyrimidinyl, pyrazolyl, benzo[b]thiophenyl, thiazolo[3,2-b][1,2,4]-triazolyl, pyrrolyl, quinolinyl, isoquinolinyl, 1,2,3,4-tetrahydroquinolinyl, benzoimidazolyl, indolyl or 1,3-benzodioxolyl;

heterocyclyl is 2-oxoazepanyl, tetrahydrofuranyl, 1,3-dioxolanyl, morpholinyl, pyrrolidinyl, piperazinyl or piperidinyl;

or a physiologically tolerated salt thereof.

5. A compound according to claim 1, wherein:

A is $CR^3$;

B is N;

D is $CR^5$;

E is $CR^6$;

$R^1$ is pyridin-4-yl, 2-ethylaminopyrimidin-4-yl, 2-(2-morpholin-4-ylethylamino)-pyrimidin-4-yl, 2-methylaminopyrimidin-4-yl, 6-methyl-2-(2-morpholin-4-ylethylamino)pyrimidin-4-yl, 2-(1-phenylethylamino)pyrimidin-4-yl, 3-methoxy-4-hydroxyphenyl or 4-butylaminopyrimidin-4-yl, $R^2$ is hydrogen;

$R^3$, $R^4$, $R^5$ and $R^6$ are independently of one another selected from the group consisting of:

hydrogen, fluorine, chlorine, bromine, —CN, —C(O)NH(2-cyclohexyl-aminoethyl-), —C(O)NH(3-(4-methylpiperazin-1-yl)propyl-), —C(O)NH(3-hydroxypropyl-), —C(O)NH(3-cyclohexylaminopropyl-), methyl, ethyl and trifluoromethyl;

or a physiologically tolerated salt thereof.

6. A compound according to claim 1, selected from 4-(3H-imidazol[4,5-c]pyridin-2-yl)-6-pyridin-4-yl-2H-pyridazin-3-one;

or a physiologically tolerated salt thereof.

7. A pharmaceutical composition comprising an effective amount of at least one compound or a physiologically tolerated salt thereof according to claim 1 and a physiologically tolerated carrier.

8. A pharmaceutical composition as claimed in claim 7, where the pharmaceutical composition is in the form of a pill, tablet, coated tablet, lozenge, granule, capsule, hard or soft gelatin capsule, aqueous solution, alcoholic solution, oily solution, syrup, emulsion, suspension, suppository, pastille, solution for injection or infusion, ointment, tincture, cream, lotion, powder, spray, transdermal therapeutic systems, nasal spray, aerosol, aerosol mixture, microcapsule, implant, rod or patch.

9. A pharmaceutical composition comprising an effective amount of at least one compound or a physiologically tolerated salt thereof according to claim 6 and a physiologically tolerated carrier a physiologically tolerated carrier.

10. A pharmaceutical composition as claimed in claim 9, where the pharmaceutical composition is in the form of a pill, tablet, coated tablet, lozenge, granule, capsule, hard or soft gelatin capsule, aqueous solution, alcoholic solution, oily solution, syrup, emulsion, suspension, suppository, pastille, solution for injection or infusion, ointment, tincture, cream, lotion, powder, spray, transdermal therapeutic systems, nasal spray, aerosol, aerosol mixture, microcapsule, implant, rod or patch.

11. A compound selected from the group consisting of 6-chloro-4-(3H-imidazo[4,5-c]pyridin-2-yl)-2H-pyridazin-3-one and 4-(3H-imidazol [4,5-c]pyridin-2-yl)-6-pyridin-4-yl-2H-pyridazin-3-one; or a physiologically tolerated salt thereof.

12. A pharmaceutical composition comprising an effective amount of a compound or a physiologically tolerated salt thereof according to claim 11 and a physiologically tolerated carrier.

* * * * *